(12) United States Patent
Portinga et al.

(10) Patent No.: US 11,786,619 B2
(45) Date of Patent: Oct. 17, 2023

(54) ULTRAVIOLET RADIATION LIGHTING DEVICE

(71) Applicant: Troy—CSL Lighting Inc., City of Industry, CA (US)

(72) Inventors: Joshua Portinga, Chino Hills, CA (US); Calvin Wong, Diamond Bar, CA (US); Steve Nadell, City of Industry, CA (US)

(73) Assignee: Troy-CSL Lighting Inc., City of Industry, CA (US)

( * ) Notice: Subject to any disclaimer, the term of this patent is extended or adjusted under 35 U.S.C. 154(b) by 210 days.

(21) Appl. No.: 17/375,980

(22) Filed: Jul. 14, 2021

(65) Prior Publication Data

US 2022/0016284 A1  Jan. 20, 2022

Related U.S. Application Data

(60) Provisional application No. 63/052,827, filed on Jul. 16, 2020.

(51) Int. Cl.
*A61L 2/10* (2006.01)
*A61L 9/20* (2006.01)

(52) U.S. Cl.
CPC .................. *A61L 2/10* (2013.01); *A61L 9/20* (2013.01); *A61L 2202/25* (2013.01); *A61L 2209/12* (2013.01)

(58) Field of Classification Search
CPC .......... A61L 2/10; A61L 9/20; A61L 2202/25; A61L 2209/12
See application file for complete search history.

(56) References Cited

U.S. PATENT DOCUMENTS

| | | | |
|---|---|---|---|
| 9,370,600 B1* | 6/2016 | DuPuis | F21V 14/08 |
| 9,687,575 B2* | 6/2017 | Farren | A61L 2/10 |
| 9,724,442 B1* | 8/2017 | Munn | A61L 9/20 |
| 2009/0004046 A1* | 1/2009 | McEllen | H05B 41/39 422/2 |
| 2009/0129974 A1 | 5/2009 | McEllen | |
| 2009/0291029 A1* | 11/2009 | Ogasawara | G09F 13/00 422/122 |
| 2012/0199005 A1* | 8/2012 | Koji | F21V 17/06 96/224 |
| 2019/0070326 A1* | 3/2019 | Xie | A61L 2/26 |

* cited by examiner

*Primary Examiner* — Sean M Luck
(74) *Attorney, Agent, or Firm* — Foley & Lardner LLP

(57) ABSTRACT

A fixture system includes a housing configured to be mounted in an upper region of a room or area. A light source is supported by the housing for providing visible light to illuminate at least a portion of the room or area. An ultraviolet radiation (UVR) system is supported by the housing for emitting UVC radiation in an upper region of the room or area. The UVR system includes at least one UVC emitting source and an optic member configured to direct UVC radiation in a pattern having a vertical width dimension that is above a threshold height from a floor or ground in the room or area.

20 Claims, 14 Drawing Sheets

ULTRAVIOLET RADIATION LIGHTING DEVICE

CROSS-REFERENCE TO RELATED APPLICATIONS AND CLAIM OF PRIORITY

This application claims the benefit of U.S. Provisional Application No. 63/052,827, filed Jul. 16, 2020, the content of which are fully incorporated herein by reference in its entirety.

BACKGROUND

Ultraviolet radiation (UVR), in certain wavelengths and intensities, can be an effective disabler of certain bacteria and viruses (or pathogens), including airborne pathogens. Ultraviolet C (UVC) radiation is often defined as having a wavelength of between 200 and 280 nanometers (nm) and has been used as an anti-pathogen or decontamination agent in various contexts. (Some sources define UVC as low as 100 nm or as high as 290 nm.) For example, UVC radiation has been used in water treatment plants and for decontamination of surgical tools, hospital rooms and other medical facilities.

UVC radiation can be an effective anti-pathogen in many environments, including, but not limited to medical facilities, classroom or school buildings, workplace buildings, airports, train stations, bus stations, grocery stores, concert halls and other public or private buildings or locations. However, due to possible adverse effects from direct exposure of UVC radiation with the skin or eyes of people or animals, UVC radiation systems are typically used in locations that are separated from or temporally vacated of people or animals during the UVC exposure. For example, typical dedicated UVC sanitation systems may be installed in operating rooms for use between surgical procedures, or in business facilities for use during business closure hours, when no people are present in the environment to be sanitized.

Accordingly, while certain UVC sanitation systems can provide sanitation operations intermittently, they may not be safely operated during periods of time in which people or animals are present. In addition, certain UVC sanitation systems require installation of one or more dedicated UVC radiation devices that sufficiently cover an area designated for sanitation.

SUMMARY

Example embodiments described herein relate to a fixture system including a housing configured to be mounted in an upper region of a room or area, a light source supported by the housing for providing visible light to illuminate at least a portion of the room or area, and an ultraviolet radiation (UVR) system supported by the housing for emitting UVC radiation having one or more wavelengths within the range of 200 nm. to 290 nm. in an upper region of the room or area.

In further examples, the light source is supported by the housing to emit visible light in a downward direction or downward angled direction within the room or area and the UVR system is supported by the housing to emit the UVC radiation in a horizontal direction or in an upward angled direction within the room or area.

In further examples, the UVR system includes at least one UVC emitting source and an optic member configured to direct the UVC radiation from the at least one UVC emitting source in a pattern having a vertical width dimension that is above a threshold height from a floor or ground in the room or area.

In further examples, the UVR system includes at least one UVC emitting source.

In further examples, the UVR system includes an optic member and a circuit board, the circuit board has a substrate on which a plurality of UVC emitting LEDs are mounted for emitting the UVC radiation toward the optic member, and the optic member is configured to emit the UVC radiation in a horizontal direction or in an upward angled direction within the room or area.

In further examples, the system further includes a bracket attached to the housing and configured to receive and hold the circuit board of the UVR system, where the bracket is configured to allow selective removal of the circuit board from the bracket for service, inspection or replacement.

In further examples, the housing has a first end having an opening or optical passage arranged to pass light from the light source, the housing has a second end on which the bracket is attached, and the second end of the housing faces opposite to the first end of the housing, In further examples, the system further includes a shaft for supporting the housing from a ceiling, wall or other structure, where the circuit board extends partially around the shaft and has a gap to pass the shaft as the circuit board is moved into or out from the bracket.

In further examples, the system further includes a shaft for supporting the housing from a ceiling, wall or other structure, where the shaft extends in a direction of an axis A of the housing, and where the circuit board is selectively moveable into or out of the bracket in a direction that is transverse to the axis A.

In further examples, the UVR system is configured to be selectively added onto or removed from the housing, as an add-on accessory.

In further examples, the optic member and the circuit board of the UVR system are attached together as to form a one-piece, unitary structure that can be selectively added onto or removed from the housing.

In further examples, the optic member includes a body of quartz, fused quartz, or fused silica.

In further examples, the circuit board of the UVR system further includes at least one light emitting source for emitting visible light in a horizontal direction or in an upward angled direction within the room or area.

In further examples, the UVR system includes at least one UVC emitting source and an optic member configured to direct the UVC radiation from the at least one UVC emitting source in a pattern having a vertical width dimension that is above a threshold height from a floor or ground in the room or area.

In further examples, the UVR system includes a circuit board on which at least one UVC emitting device is mounted, where the circuit board is in thermal communication with the housing to transfer heat from the UVC emitting device to the housing for dissipation in or from the housing.

In further examples, the light source is supported in the housing to emit visible light in a downward direction or downward angled direction within the room or area and where the light source is in thermal communication with the housing to transfer heat from the light source to the housing for dissipation in or from the housing.

In further examples, the system further includes a flange member on a first end of the housing, where the housing is configured to be received within a hole in a ceiling, in a wall or in another structure, while the flange member is located on an exposed side of the ceiling, of the wall or of the other structure, and where the UVR system is attached to the flange member.

In further examples, the system further includes a fan motor and fan blades supported by the housing below the UVR system.

Further examples relate to a fixture system including a housing configured to be mounted in an upper region of a room or area, an ultraviolet radiation (UVR) system supported by the housing and having at least one UVR emitting source and an optic member for emitting UVC radiation in an upper region of the room or area, in a horizontal direction or in an upward angled direction within the room or area, and a flange member on a first end of the housing. The housing is configured to be received within a hole in a ceiling, in a wall or in another structure, while the flange member is configured to be located on an exposed side of the ceiling, of the wall or of the other structure. The UVR system is attached to the flange member to be located on the exposed side of the ceiling, of the wall or of the other structure.

In further examples, that system further includes a baffle member attached to the UVR system to block the UVC radiation and visible light from passing in a vertical direction relative to the UVR system, where the UVR system further includes at least one a light source configured to emit visible light in the horizontal direction or in the upward angled direction within the room or area, above the baffle member.

BRIEF DESCRIPTION OF THE DRAWINGS

The above and other aspects and features of the present invention will become more apparent to those skilled in the art from the following detailed description of the example embodiments with reference to the accompanying drawings, in which.

DETAILED DESCRIPTION

Figure 1:
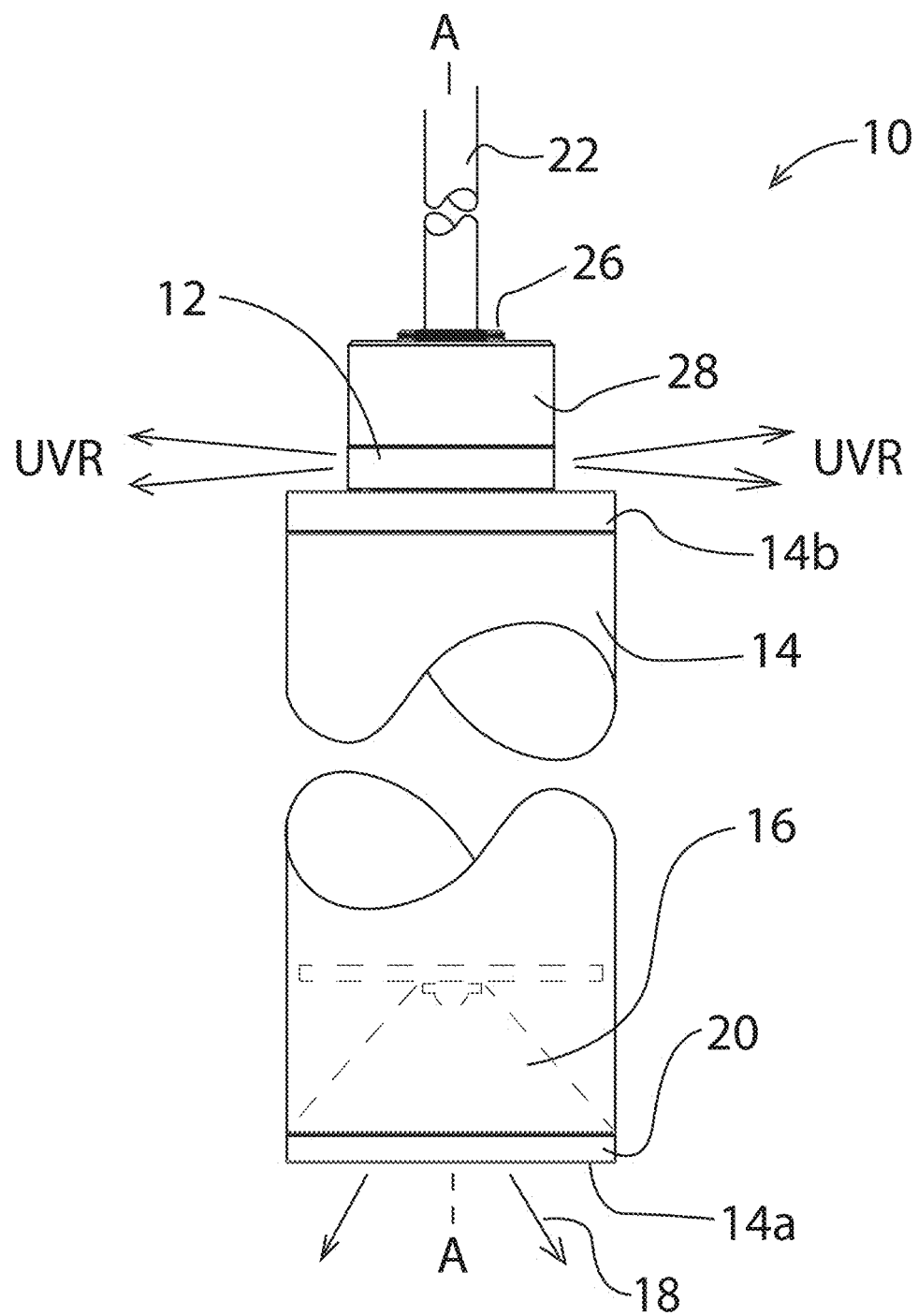
FIG. 1 is a side view of a light fixture having a UVR system according to an example embodiment.
Figure 2:
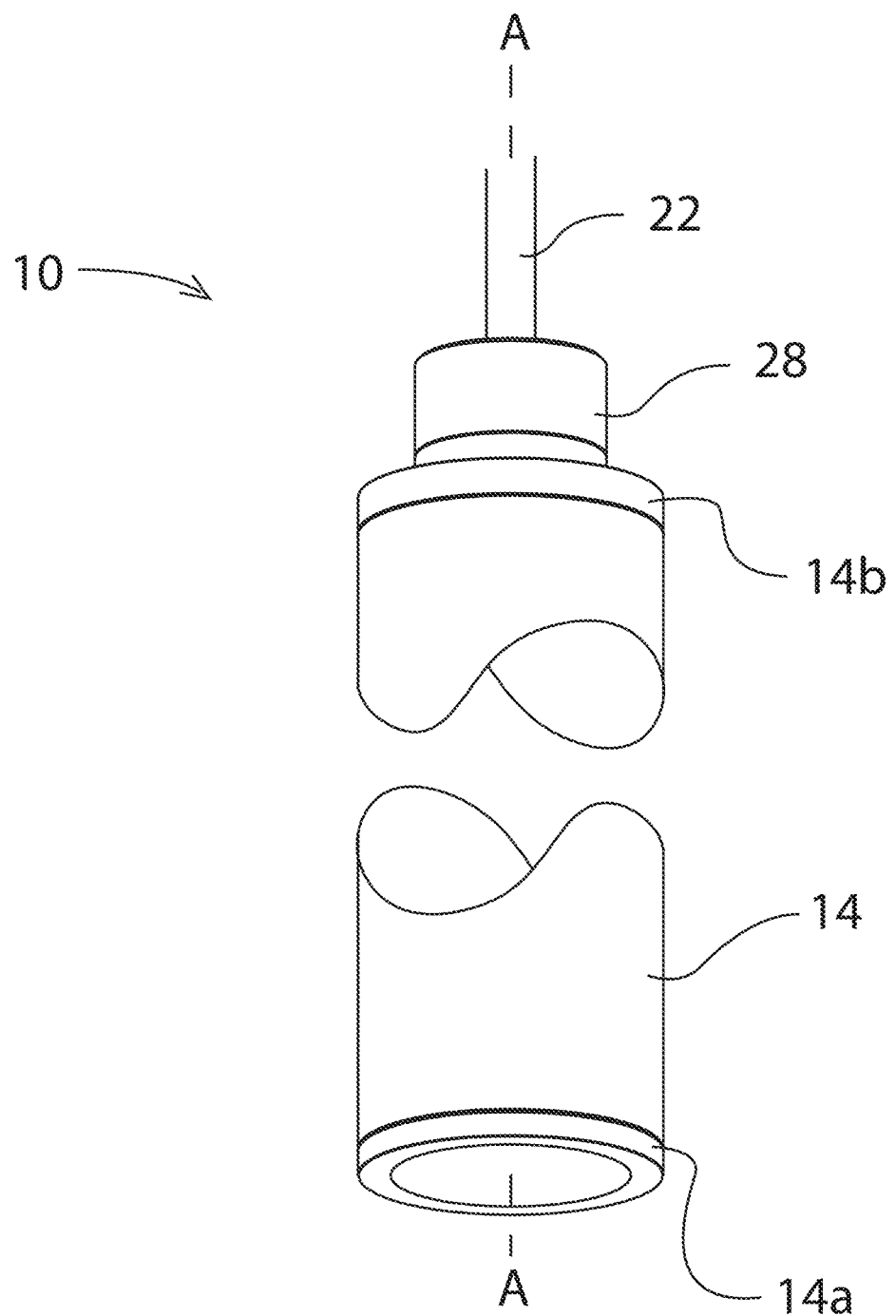
FIG. 2 is a perspective view of a light fixture according to the example of FIG. 1.
Figure 3:
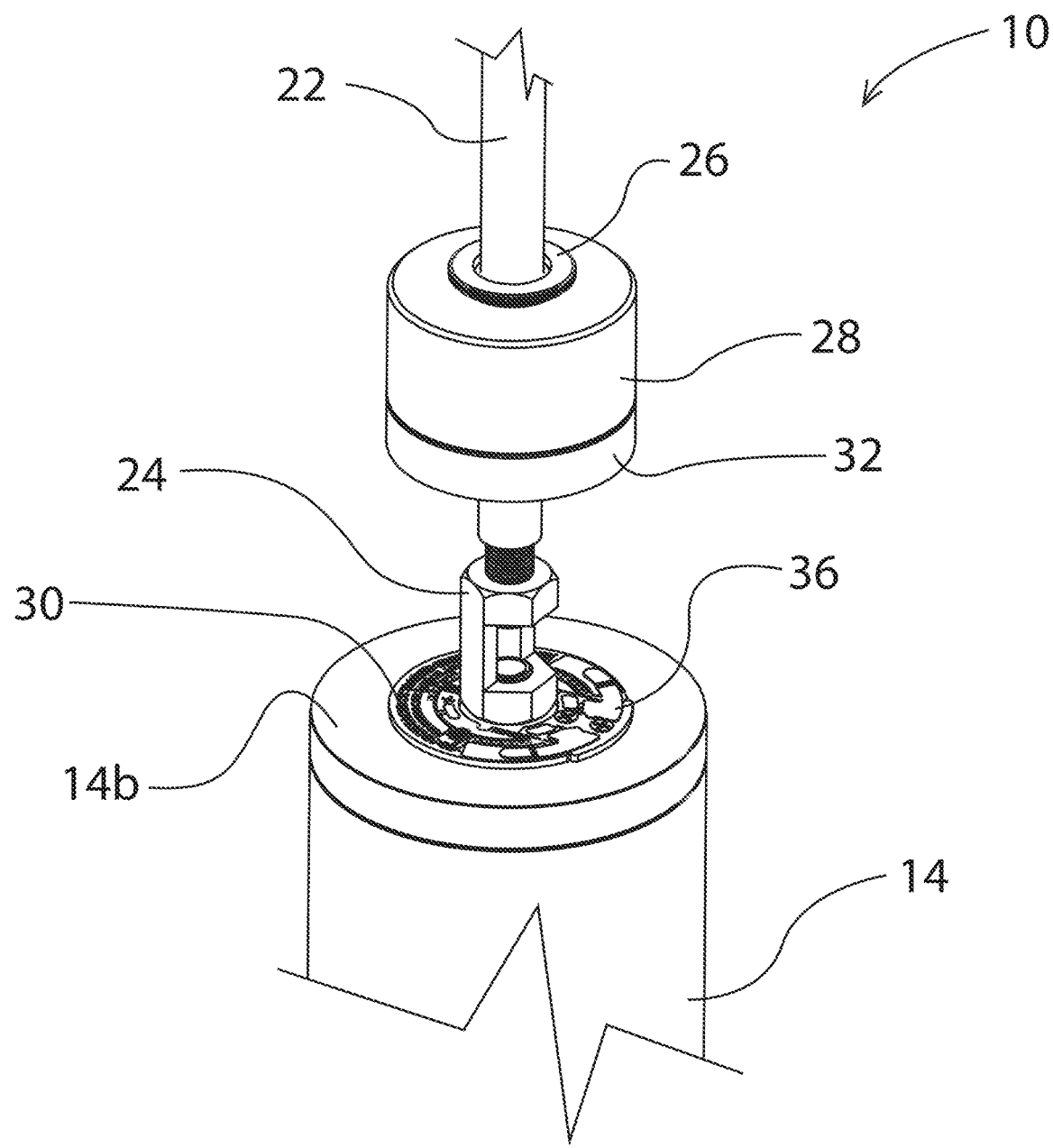
FIG. 3 is a perspective, partially exploded view of a portion of the light fixture of FIG. 1.
Figure 4:
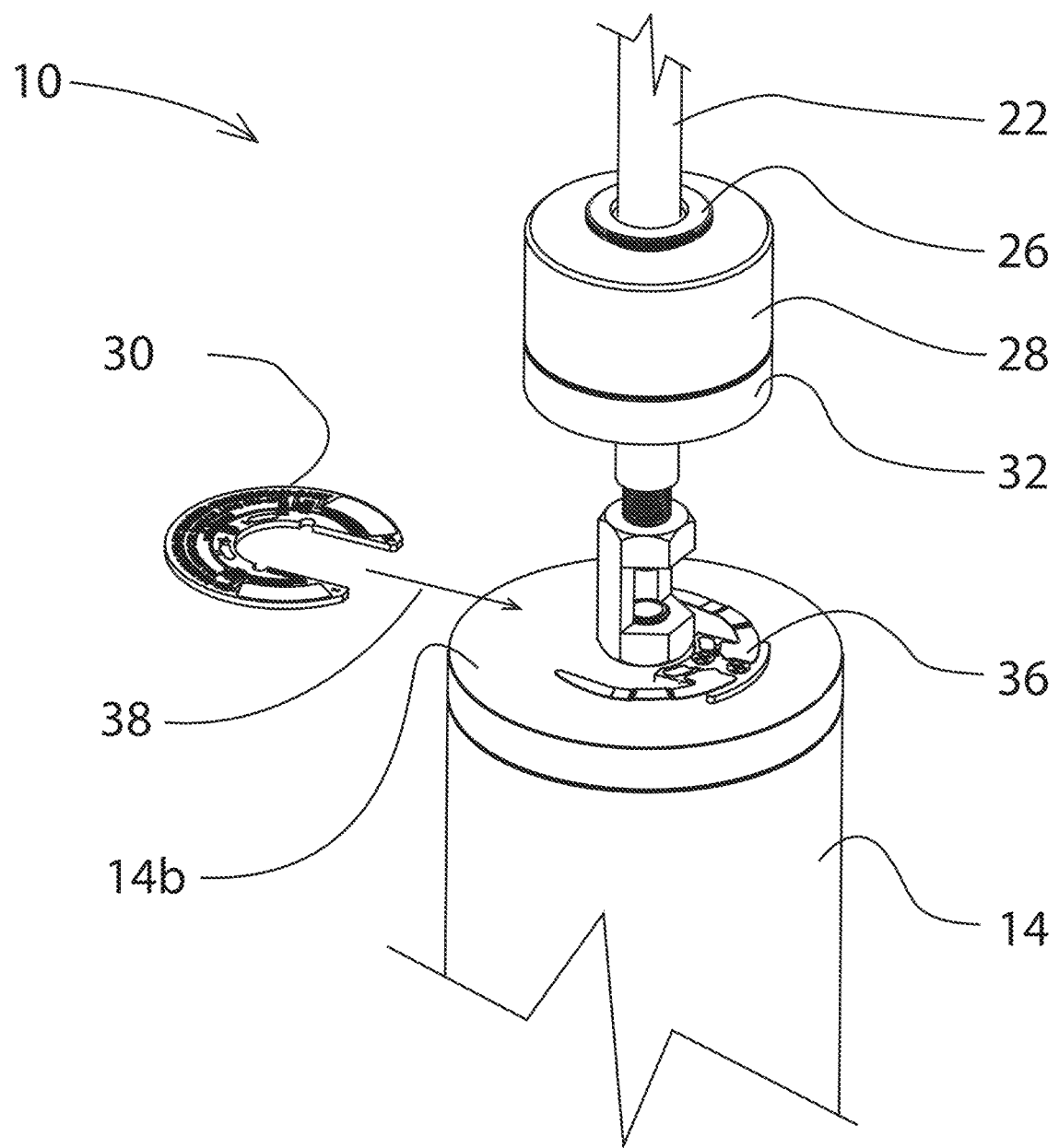
FIG. 4 is a further perspective, partially exploded view of a portion of the light fixture of FIG. 1.
Figure 5:
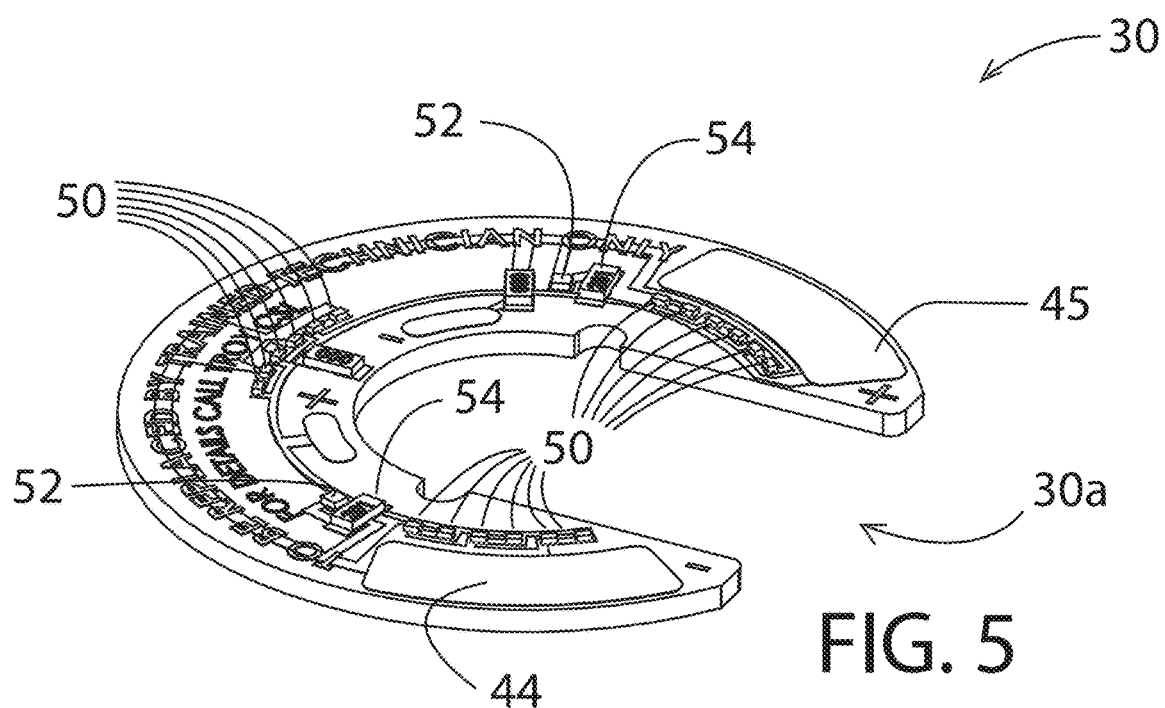
FIG. 5 is a perspective view of an example of a circuit board of a UVR system for the light fixture of FIG. 1.

Hereinafter, example embodiments are described in more detail with reference to the accompanying drawings. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated. Further, features or aspects within each example embodiment should typically be considered as available for other similar features or aspects in other example embodiments.

In the drawings, the relative sizes of elements, layers, and regions may be exaggerated and/or simplified for clarity. Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

It will be understood that when an element or layer is referred to as being "on," "connected to," "coupled to," "secured to" or "attached to" another element or feature, it can be directly on, connected to, coupled to, secured to or attached to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," "has," "have," and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "generally," "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" or "example" is intended to refer to an example embodiment or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

A typical room or area in which people or animals may be present can have one or more (or a plurality) of light fixtures at spaced locations, to provide visible light within the room or area and illuminate the room or area (or portions thereof). Modern buildings are typically built to include one or more (or a plurality of) light fixtures in rooms, lobbies, hallways and other areas, and are wired with suitable electrical conductors to provide electrical power to the light fixtures. In typical buildings and other facilities, light fixtures may be mounted on (from or in) a ceiling, rafter or other structure in the upper region of a room or area of the building or facility. Air may be circulated within a building or other facility (for example, due to natural circulation characteristics of the room or area or due to additional air circulation systems) and, as a result, may circulate from upper regions to lower regions (and vice versa) of rooms or other areas of the building or facility.

Certain example UVR systems described herein are configured to be included in a light fixture, ceiling fan fixture or other fixture, as part of the fixture (e.g., built into the fixture as part of the original manufacture of the fixture). Other example UVR systems described herein are configured to be included in a light fixture, ceiling fan or other fixture, as an add-on or accessory that can be selectively added (or not) to the fixture.

In particular examples described herein, a light fixture has one or more lighting devices configured to emit visible light (within a portion of the visible light spectrum) downward or outward, to illuminate the room or area (or a portion thereof), but also includes a UVR system to emit UVC radiation in an upper region of an area or room. In further examples, a ceiling fan fixture has a fan motor, fan blades and, in some examples, one or more lighting devices configured to emit visible light downward or outward, where the ceiling fan fixture also includes a UVR system to emit UVC radiation in an upper region of an area or room. In further examples, a UVR system fixture has a housing configured to be installed within a ceiling, wall or other structure in a manner similar to the manner in which a downlight fixture is installed, and may include or resemble a downlight fixture, where the UVR system is configured to emit UVC radiation in an upper region of an area or room.

In those examples, the UVR system may be configured to be supported in the fixture, in an upper region of a room or area, and to emit UVC radiation in a direction and in a pattern that is above and over the height of a human (such as above the visible light emitting device of the light fixture, or above the fan blades of the ceiling fan). In certain examples, the UVR system is configured to emit UVC radiation substantially horizontally (about 90 degrees from a vertical axis) or angled toward the ceiling (for example, at an angle that is greater than 45 degrees and less than 90 degrees from a vertical axis, or other suitable angles including angles directed downward or slightly downward). In certain examples, the UVR system is configured to emit UVC radiation in a pattern that is relatively wide in a horizontal direction and relatively narrow in the vertical direction, and confined to an upper region of a room or area. In some examples, the UVR system is configured to emit UVC radiation in a direction that is at an angle (or slight angle) toward the ceiling, to further avoid direct exposure of UVR on people or animals in the room space. In those or other examples, the UVR system is configured to emit UVC radiation within a wavelength of 200 nm. to 230 nm. and in a direction that is at an angle (or slight angle) downward, away from the ceiling.

In some examples, the UVR systems may be electrically connected to electrical power conductors typically provided in a building or facility for light fixtures, ceiling fans or the like (typically at locations designated or desirable for light fixtures, ceiling fans or the like). In other examples, the UVR systems electrically connect to separate electrical power conductors (or a separate electrical circuit) relative to electrical power conductors that are designated for connecting to light fixtures, ceiling fans or other fixtures.

An example of a light fixture 10 having a UVR system 12 is described with reference to FIGS. 1-7. The light fixture 10 includes an outer housing 14 that contains a lighting device 16. The lighting device 16 is configured for producing a visible light output 18 from one end 14a of the outer housing 14.

The light fixture 10 is configured to be installed in an upper region of a room or area, for example from a ceiling, rafter or other structure over the room or area space. When the light fixture 10 is installed with the axis A generally vertical, the visible light output 18 is directed outward and downward to illuminate a portion of a room or area below the light fixture 10. In some examples, the light output 18 may be emitted in a direction and pattern that is centered or symmetrical relative to the axis A, or that is angled or offset relative the axis A. In other examples, the light output 18 may be emitted in a direction or pattern that is adjustable relative to the axis A or one or more other axes transverse to axis A.

The lighting device 16 may include a light source having one or more light emitting devices such as, but not limited to one or more LED, incandescent, halogen, fluorescent, or other electronic light emitting devices, combinations thereof, or the like. In certain examples, the lighting device 16 and outer housing 14 of the lighting fixture 10 in FIGS. 1-7 may be configured in accordance with the lighting device assembly 1106 and the housing member 1102 of the lighting device 1100 shown in FIGS. 11A and 11B in published U.S. patent application Ser. No. 16/175,470, publication no. 2020/0132278 A1 (which is incorporated herein by reference, in its entirety). In certain other examples, the lighting device 16 and the outer housing 14 of the lighting fixture 10 in FIGS. 1-7 may be configured in accordance with the lighting device module 1950 and the housing 1960 of the lighting device assembly 1900 shown in FIGS. 19-21 in U.S. patent application Ser. No. 16/808,102 (which is incorporated herein by reference, in its entirety). In yet other examples, the lighting device 16 and the outer housing 14 may have other suitable configurations.

The outer housing 14 in the example shown in FIGS. 1-4 has a generally cylindrical shape along an axis A, and may have a hollow or partially hollow interior in which the lighting device 16 is located. The outer housing 14 may have any suitable length dimension (along the axis A), as represented by the break in the drawing of the outer housing 14. In other examples, the outer housing 14 may have other suitable shapes, including, but not limited to spherical or partially spherical shapes, conical or pyramidal shaped, cylindrical shaped with a curved or polygonal cross-section shape taken perpendicular to the axis A, or the like.

In certain examples, the outer housing 14 includes an end cap or flange member 20 that is securable at the end 14a, to retain the lighting device 16 within the outer housing 14 or to provide a decorative end on the outer housing 14 (or both). The end cap or flange 20 may have an opening or optical passage through which light from the lighting device 16 may pass and be emitted into a room or area. In certain examples, the outer housing 14 may include a second end cap 21 selectively or permanently secured at a second end 14b of the outer housing 14, for example, to facilitate manufacture of the housing 14 or assembly of the light fixture 10 (or both). In other examples, one or both of the end caps 20 and 21 may be omitted, or may be integrally formed as part of the outer housing 14.

The outer housing 14 including the end caps 20 and 21 may be made of any suitable material or materials having sufficient rigidity and strength to function as described herein including, but not limited to metal, plastic, ceramic, wood, composite material, or combinations thereof. In particular examples, the outer housing 14 including the end caps 20 and 21 are made of one or more metal materials or other materials having good thermal conductivity to operate as a heat sink and receive, conduct and quickly dissipate heat generated by the lighting device 16 or the UVR system 12 (or both). In certain examples, the outer housing 14 may be configured to have a relatively significant mass of thermally conductive material, to help improve its heat dissipation characteristics.

The light fixture 10 in FIGS. 1-4 also includes a shaft or pole 22 for supporting the outer housing 14, for example, from a ceiling, rafter, or other structure over a room or area space. A threaded connector 24 (or lamp reducer or hickey) may be fixed to, and extend from a second end 14b of the outer housing 14. A correspondingly threaded nut 26 may be provided on the shaft 22, for connecting the shaft 22 to the connector 24 and, thus, to the outer housing 14. The light fixture 10 may include a hollow, tubular collar 28 located between the threaded nut 26 and the outer housing 14 and through which a portion of the connector 24 extends. The shaft 22, the connector 24, and the collar 28 may be made of any suitable materials having sufficient rigidity and strength to function as described herein including, but not limited to metal, plastic, ceramic, wood, composite material, or combinations thereof.

In particular examples, each of the shaft 22 and the connector 24 have a hollow interior through which electrical conductors (not shown) extend for providing electrical power or control signals (or both) to the lighting device 16 or the UVR system 12 (or both). Those electrical conductors may be configured to connect to existing or installed electrical conductors in a building or area in which the light fixture 10 is to be installed.

When installed, the shaft 22 may be connected to a ceiling, rafter or other structure in an upper region of a room or area, to support the outer housing 14 in a generally vertical orientation along the axis A, within the upper region of the room or area (for example, as a pendant fixture). In other examples, the shaft 22 and the threaded nut 26 may be omitted, and the outer housing 14 may be configured to mount to a surface of a ceiling, rafter or other structure in an upper region of a room or area space, directly, through the connector 24, the collar 28 or a further mounting member.

The UVR system 12 is located between the collar 28 and the outer housing 14. The UVR system 12 includes a UVR circuit board 30 and an optic member 32 (each described below). The UVR circuit board includes one or more UVR emitting devices and other electronics (as described herein). The optic member 32 of the UVR system 12 and the collar 28 may be secured in place by sufficiently tightening the threaded nut 26 onto the connector 24. In certain examples, a bias member 34 such as, but not limited to a spring washer may be located between the collar 28 and an optic member 32 of the UVR system 12, to impart a bias force on and between the collar 28 and the optic member 32 when the threaded nut 26 is tightened onto the connector 24. In other examples, the bias member 34 may be omitted.

In certain examples, a bracket 36 is provided to hold the UVR circuit board 30 or provide electrical connections to the UVR circuit board 30 (or both). In the example in FIGS. 1-7, the bracket 36 is mounted to the second end 14b of the outer housing 14, and secures the UVR circuit board 30 to the second end 14b of the outer housing 14. In particular examples, when the UVR circuit board 30 is secured to the second end 14b of the outer housing 14 by the bracket 36, the UVR circuit board 30 is held in direct contact (or in other suitable heat transfer communication) with the second end 14b of the outer housing 14, to allow transfer of heat from the UV sources and other electronics on the UVR circuit board 30 to the outer housing 14. Accordingly, heat transferred from the UV sources and other electronics may be dissipated through and from the outer housing 14. In certain examples, the bias member 34 imparts a bias force on the UVR circuit board, through the optic member 32, to help urge the UVR circuit board 30 against and in heat transfer contact or communication with the second end 14b of the outer housing 14.

In certain examples, the UVR circuit board 30 (or one or more circuit components on the circuit board 30) may have an operational life span that is shorter than the operational life span of the lighting device 16 and other components of the lighting fixture 10, such that replacement of the UVR circuit board 30 one or more times during the operational life span of the lighting fixture may be desired. Accordingly, in certain examples, the UVR circuit board 30 and the bracket 36 are configured to allow the circuit board 30 to be selectively installed in and removed from the bracket 36, for inspection, maintenance or replacement of the circuit board 30.

In particular examples, the threaded nut 26 may be loosened sufficiently to allow the collar 28 and the optic member 32 to be lifted or separated from the end 14b of the outer housing 14 by a sufficient amount to allow access to UVR circuit board 30 or the bracket 36 (or both), to allow selective installation or removal of the UVR circuit board 30. The UVR circuit board 30 may be configured to extend at least partially around the connector 24 (and the axis A), when the circuit board 30 is held within the bracket 36. In particular examples, the UVR circuit board 30 has a gap 30a on one side, to pass the connector 24 during installation or removal of the circuit board 30 in or from the bracket 36. In some examples, the UVR circuit board 30 has a generally "C" shape as shown in the drawings. In other examples, the UVR circuit board 30 has other suitable shapes with a gap 30a.

The gap 30a may be configured to allow the UVR circuit board 30 to be slid (e.g., manually or with a tool) into or out from the bracket 36 in a direction of the arrow 38, transverse (or perpendicular) to the direction of the axis A, for selective installation or removal of the circuit board 30 into or out of the light fixture 10. Once the UVR circuit board 30 (or a replacement UVR circuit board 30) is received in the bracket 36, the optic member 32 and collar 28 may be lowered and the threaded nut 26 may be tightened to force the collar 28 (or the bias member 34) against the optic member 32. As a result, the optic member 32 may be forced against the circuit board 30 or against the bracket 36 or the second end 14a of the outer housing 14 (or a combination thereof).

Figure 6:
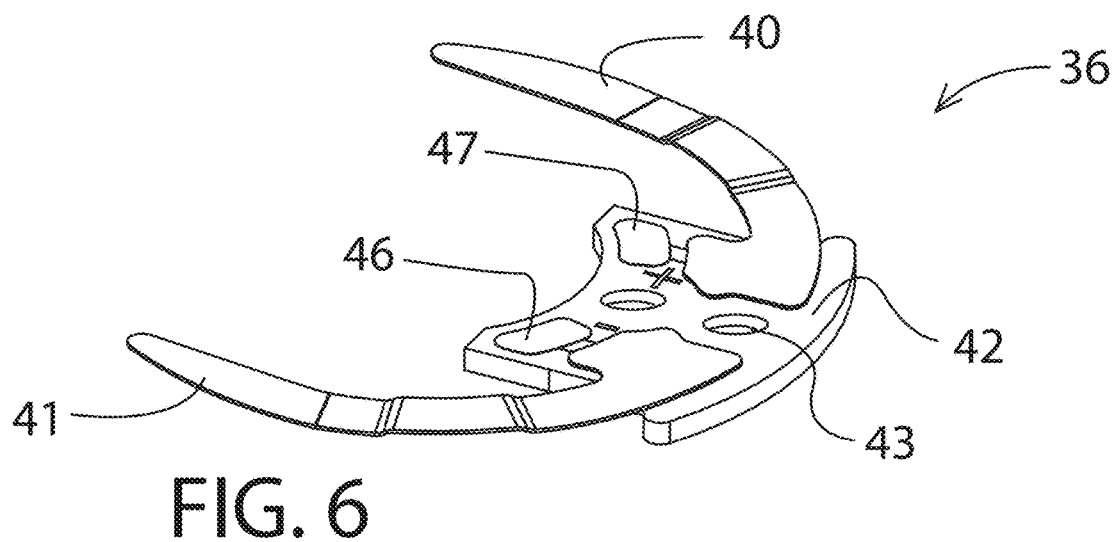
FIG. 6 is a perspective view of a bracket for a circuit board of a UVR system of the light fixture of FIG. 1.

In certain examples, the bracket 36 may include one or more arms extending from a base 42 (where the bracket example shown in FIG. 6 has two arms 40 and 41). The base 42 may be attached to the second end 14b of the outer housing 14 by one or more fastening mechanisms such as, but not limited to screws, bolts or other threaded fasteners, glue, solder, welding or other adhesives, clips, or the like. In some examples, the base 42 includes one or more openings 43 through which one or more fastening mechanisms may extend, to secure the base 42 to the second end 14b of the outer housing 14.

The arms 40 and 41 of the bracket 36 are configured to retain the UVR circuit board 30 on the second end 14b of the outer housing 14. For example, the UVR circuit board 30 may be configured to snuggly fit between the arms 40 and 41 and the second end 14b of the outer housing 14. In some examples, the arms 40 and 41 may provide electrical contact and conduction paths for contacting electrically conductive pads or other conductive parts 44 and 45 of the UVR circuit board 30. The conductive pads 44 and 45 may be electrically connected to UVR emitting devices and other electronics on the circuit board 30, through conductors on or in the circuit board substrate. Similarly, the arms 40 and 41 of the bracket 36 may be electrically connected (through conductive material on or in the base 42) to one or more electrical terminals 46 and 47 on the base 42. The terminals 46 and 47 on the base may be configured for connection to electrical wires or other conductors in the light fixture 10, for providing electrical power or control signals (or both) to the UVR circuit board 30.

The arms 40 and 41 of the bracket 36 may be made of a spring metal (or other suitable material) that imparts a bias force onto the UVR circuit board 30, to urge the UVR circuit board 30 against the second end 14b of the outer housing, to retain the UVR circuit board 30. In some examples, the second end 14b of the outer housing 14 may include a depression or groove having a shape and size sufficient to receive the UVR circuit board 30 (such as, but not limited to a shape and size corresponding to the shape and size of the circuit board 30).

The UVR circuit board 30 includes a circuit board substrate and one or more UVR emitting devices (such as, but not limited to, UVC light emitting diodes) and other electronics and electrical conductors. In various examples, the UVR emitting devices are configured to emit UVC radiation having a wavelength that provides an anti-pathogen or decontamination effect, such as one or more wavelengths within the range of 200 nm. and 280 nm. (or within the range of 100 nm and 290 nm, or 200 nm. to 290 nm). In particular examples, the UVR emitting devices emit UVC radiation having one or more wavelengths within the range of 260 nm. and 290 nm, or within the range of 270 nm. and 290 nm, as UVC within those ranges of wavelengths has been found to provide significant anti-pathogen or decontamination effects. In particular examples, the UVR emitting devices emit UVC radiation having one or more wavelengths within the range of 200 nm. and 230 nm, as UVC within that range of wavelengths has been found to provide significant anti-pathogen or decontamination effects and can avoid or reduce detrimental effects of direct exposure to skin or eyes. In certain examples, the UVR circuit board 30 includes a plurality of UVC LEDs 50 arranged and spaced apart around the body of the circuit board 30 (to be at least partially around the axis A, when the UVR circuit board 30 is installed in the light fixture 10). In one example, the UVR circuit board 30 includes from twelve to twenty-four (or eighteen) UVC LEDs 50 spaced around the body of the circuit board 30. In other examples, the UVR circuit board 30 includes any other suitable number of UVC LEDs. In particular examples, the UVC LEDs 50 are connected in parallel (or in other electrical connection arrangements) to be activated and turned ON together or deactivated and turned OFF together.

In certain examples, the UVR circuit board 30 also includes one or more (or a plurality of) additional LEDs 52 that are configured to emit visible light (light within the visible spectrum). In some examples, two additional LEDs 52 arranged about 180 degrees apart (relative to the axis A) on the body of the circuit board 30, where each of the two additional LEDs 52 provides a visible light output (through the optic member 32) in a pattern that has about a 120 degree horizontal width, and a relatively narrow vertical width. In other examples, the UVR circuit board 30 may include any suitable number and arrangement of additional LEDs 52 to emit visible light in a desired direction and pattern.

The additional LED(s) 52 may be configured to emit visible light of any suitable color and temperature including, but not limited to white, red, violet, blue, green, yellow or combinations thereof. In some examples, the additional LED(s) 52 are arranged on the UVR circuit board 30 to emit visible light that is directed by the optic member 32 in the same general direction or pattern as the UVR from the UVC LEDs 50. In certain examples, the additional LED(s) 52 are electrically connected in parallel with the UVC LEDs 50 (or in other electrical connection) to be activated and turned ON when the UVC LEDs 50 are activated and turned ON, and to be deactivated and turned OFF when the UVC LEDs 50 are deactivated and turned OFF. In certain examples, the visible ON or OFF status of the additional LED(s) 52 can provide a visual indication that the UVC LEDs 50 (which emit UVC of a non-visible portion of the spectrum) are ON or are OFF. Alternatively or in addition, in certain examples, the visible light from the additional LED(s) 52 can provide a desirable lighting effect as descried herein.

In certain examples, the UVR circuit board 30 also includes one or more (or a plurality of) resistors or other circuit components 54 electrically connected with the LED(s) 50 or the LED(s) 52, and mounted on the same surface (first surface) of the substrate of the UVR circuit board 30 as the LED(s) 50 and 52. In some examples, the resistors or other circuit components 54 have a size (height, width or both) that is larger than the size of the LED(s) 50 or the LED(s) 52 and are located on the UVR circuit board 30 in positions adjacent the LED(s) 52, or between the LED(s) 52 and adjacent UVC LED(s) 50, to provide a light-blocking barrier or shield that shields the LED(s) 52 from radiation emitted by the UVC LED(s) 50. In that regard, the resistors or other circuit components 54 may be arranged on the UVR circuit board 30 in positions that help to shield the LED(s) 52 from UVC radiation that may otherwise harm the LED(s) 52 or shorten the operable life span of the LED(s) 52. In other examples, other suitable shield structures may be provided on the circuit board 30, between the LED(s) 52 and UVC LED(s) 50, to provide a light-blocking barrier or shield that shields the LED(s) 52 from radiation emitted by the UVC LED(s) 50.

Figure 7:
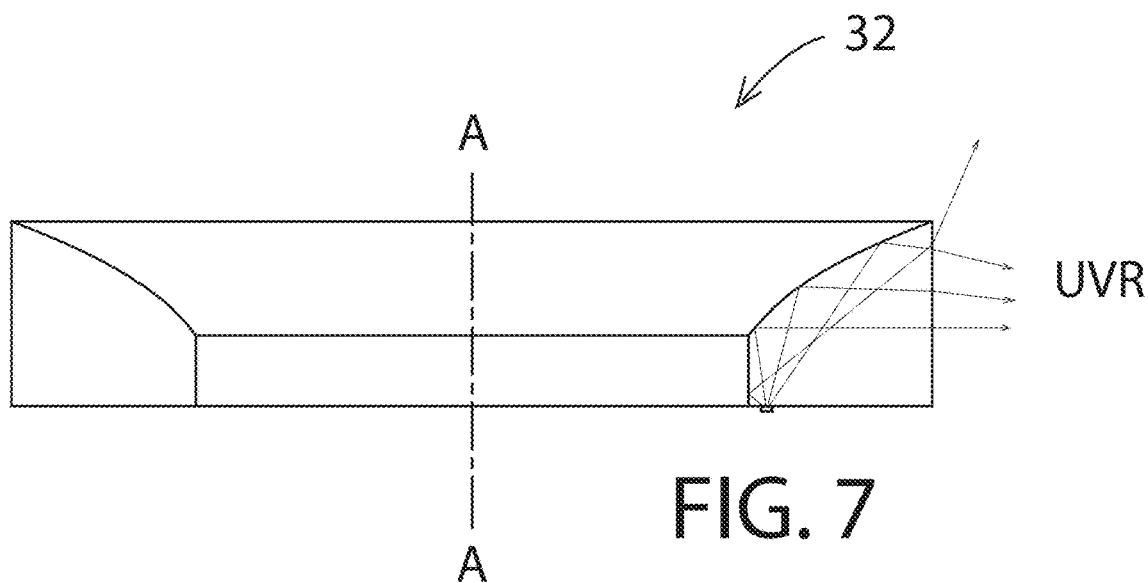
FIG. 7 is a side, schematic view of an optic member of a UVR system for the light fixture of FIG. 1.

The LED(s) 50 and 52 are mounted on the first surface of the UVR circuit board 30 and are arranged to emit radiation toward the optic member 32. An example of an optic member 32 is shown in FIG. 7. The optic member 32 is configured to receive UVR from the one or more UVR emitting devices (e.g., LED(s) 50), and to direct the UVR in one or more desired directions and in a first desired pattern. The optic member 32 has a receiving side (facing downward in FIG. 7) that is arranged to face the UVR circuit board 30, and through which UVR from the UVR emitting devices 50 and visible light from the light emitting devices 52 is received.

Figure 8:
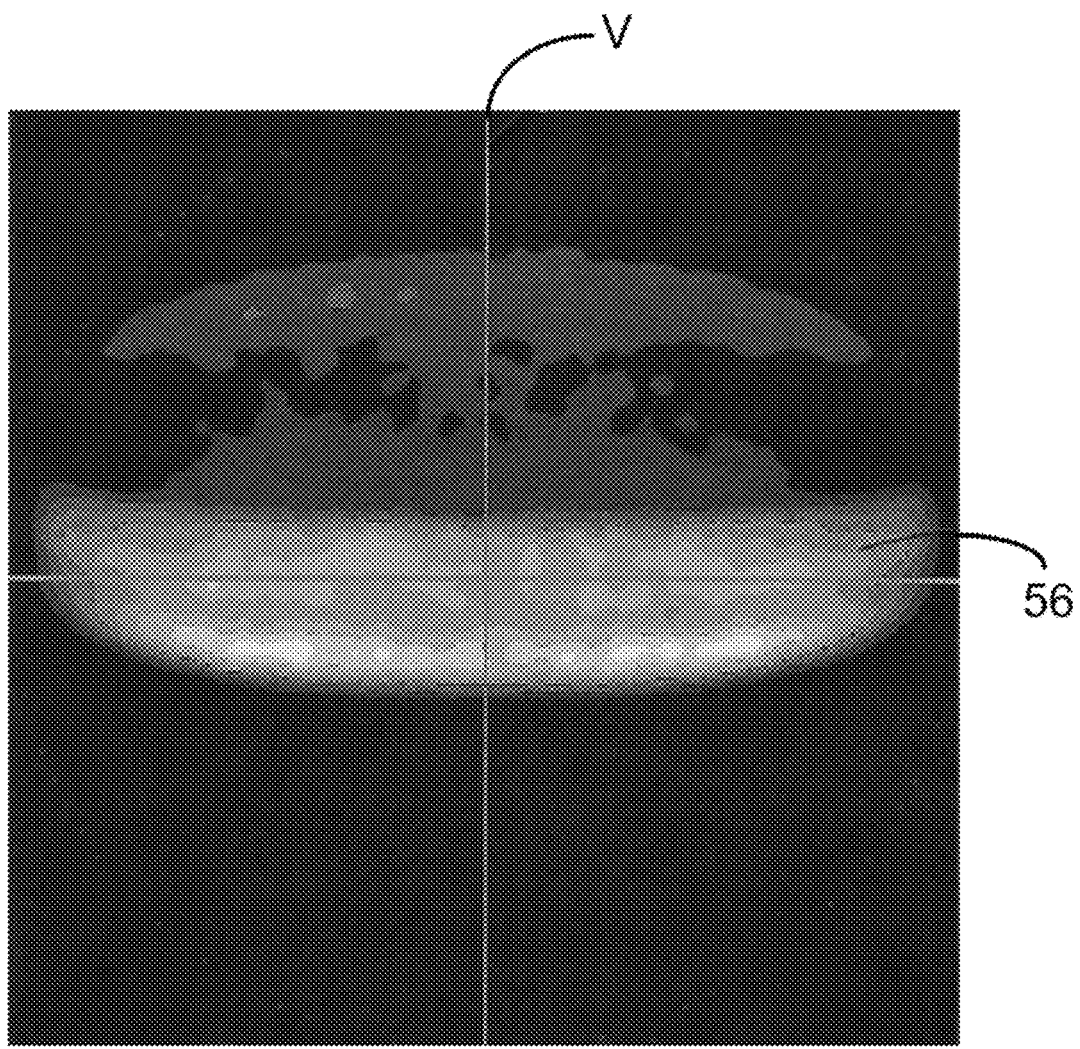
FIG. 8 is a computer-generated view of an example of a UVR pattern provided by a UVR system for the light fixture of FIG. 1.

In particular examples, the optic member 32 emits the UVR in a direction that is generally horizontal (or transverse to the direction of the axis A), in a pattern that is relatively wide in the horizontal direction, and contained within a relatively narrow width in the vertical direction. In particular examples, when the fixture 10 is installed in a room or area, the pattern of UVR emitted by the optic member 32 is contained in a volume space located above the first end 14a of the outer housing 14 of the light fixture 10. In other examples, the optic member 32 emits the UVR in a direction that is at an angle relative to the horizontal direction (between 0 degrees and 45 degrees) toward the ceiling. An example of a first pattern 56 of UVR emitted from the optic member 32 is shown in FIG. 8. The vertical line V in FIG. 8 is parallel to the axis A of the installed fixture 10.

In addition, the optic member 32 is configured to receive visible light from the one or more visible light emitting devices (e.g., LED(s) 52), and to direct the visible light in one or more desired directions and in a second desired pattern. In certain examples, the one or more desired directions of the visible light and the second desired pattern approximates or is similar to the one or more desired directions of the UVR and the first desired pattern. In other examples, the desired direction and pattern of the visible light is different from those of the UVR.

In certain examples, the optic member 32 is a light guide that receives UVR and visible light on the receiving side (e.g., the side facing downward and in the direction of axis A in FIG. 7), and emits the UVR and visible light from a different side (e.g., a lateral or peripheral side) in a direction generally horizontal or transverse to the axis A. In other examples, the optic member 32 is a reflector that receives UVR and visible light from the UVR circuit board 30 and reflects the UVR and the visible light in a direction generally horizontal or transverse to the axis A. In certain examples, the optic member 32 has an annular or ring shaped body and is configured to be located adjacent the second end 14b of the outer housing 14, with the connector 24 extending through the central opening of the annular body. In certain examples, the optic member 32 has an annular shape forming a semi-toroid shaped recess on the side facing the LEDs 50 and 52, as shown in FIG. 7. In such examples, the LEDs 50 and 52 are arranged to direct emitted radiation into the semi-toroid shaped recess of the optic member 32, and reflect the radiation in a direction transverse to the direction emitted from the LEDs 50 and 52.

In certain examples, the body of the optic member 32 is made of a material (or includes a reflective material) that is able to pass and refract (or reflect) UVR efficiently, with reduced or minimized loss of UVR intensity. Such materials include, but are not limited to fused quartz, fused silica, sapphire, certain silicones or the like. For example, the optic member 32 may be made from tube stock of fused quartz that is sliced to a desired thickness for the optic member 32 and machined to form a desired shape.

In particular examples, the shape of the optic member 32 is configured to refract or reflect UVR in a direction that is generally transverse (or perpendicular) to the axis A, to form a pattern that is relatively wide in the horizontal direction, and contained within a relatively narrow width in the vertical direction, in a volume space located above the first end 14a of the outer housing 14 of the light fixture 10 such as, but not limited to the pattern shown in FIG. 8. In certain examples, the pattern of UVR emitted from the optic member 32 encompasses a volume of a room space that is located above the height of the heads of humans or animals in the room space. In some examples, the pattern of UVR may be located above a particular height (such as, but not limited to 7 feet, 8 feet, 9 feet, or other defined height from the floor or ground of the room space), to avoid direct exposure of UVR on people or animals in the room space. In some examples, the UVR is emitted at an angle (or slight angle) toward the ceiling, to avoid direct exposure of UVR on people or animals in the room space.

In most room spaces, by locating the UVR system 12 at a height above the light output end of a light fixture 10, and directing the UVR generally perpendicular (or slightly angled toward the ceiling) relative to the axis A of the light fixture, the UVR will be directed above the height of people who may be in the room. By controlling the pattern of UVR with an optic member 32, the pattern of UVR can be emitted and concentrated in a band that is relatively narrow in the vertical direction and relatively wide in the horizontal direction, above the heads of people who may be in the room. In particular examples, the band of UVR can kill or deactivate certain airborne pathogens that are in the upper air space of a room or area, while avoiding direct UVR exposure of people or animals in the room or area.

Figure 9:
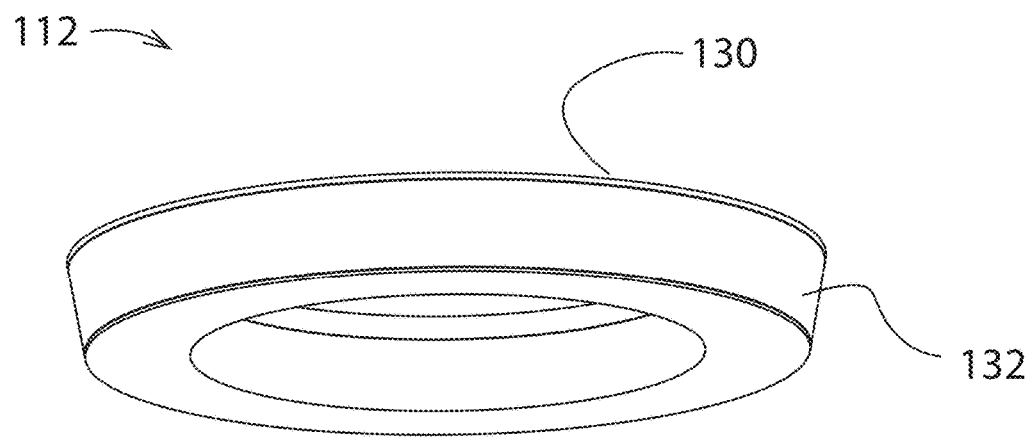
FIG. 9 is a perspective view of another example of a UVR system for the light fixture of FIG. 1 or other light fixtures.

In the example of FIGS. 1-7, the UVR system 12 is part of, or installed in the light fixture 10. In further examples, a UVR system 112 may be configured as an add-on accessory that can be installed on or in light fixtures of a certain type or of many different types. In some examples, the UVR system 112 may include a UVR circuit board connected together with an optic member to form an integrated and unitary device that can be selectively installed in a light fixture. For example, as shown in FIG. 9, the UVR system 112 has an annular or ring-shaped body that includes a UVR circuit board 130 and an optic member 132 connected together (or housed together in a common housing) as an integrated and unitary structure. The UVR circuit board 130 and the optic 132 may be similar to or correspond to the UVR circuit board 30 and the optic member 32, respectively, of the light fixture 10 in FIGS. 1-7.

One or more electrical contact pads or conductors may be provided on or connected to the UVR circuit board 130 of the UVR system 112, to be connected with an electrical power source. In some examples, the UVR circuit board 130 may include one or more drivers (driver electronics) for driving UVR devices and any visible light LED devices on the UVR circuit board 130. In other examples, one or more drivers (or driver electronics) may be separate from and connectable to the UVR circuit board 130, for driving LED devices on the UVR circuit board 130.

In certain examples, the UVR system 112 may be configured to be selectively installed onto (or removed from) a light fixture 10 as described in FIGS. 1-7, in place of the UVR system 12. In particular examples, the UVR system 112 may be located between the collar 28 and the second end 14b of the outer housing 14 (instead of the UVR system 12). In such examples, the UVR system 112 may be arranged on the second end 14a of the outer housing 14, with the connector 24 extending through the central opening of the annular or ring-shaped body of the UVR system 112. The collar 28 and the threaded nut 26 may be arranged on the opposite side of the UVR system 112 relative to the outer housing 14, and the threaded nut 26 may be sufficiently tightened to retain the UVR system 112 in place, within the light fixture 10. In addition, electrical power conductors may be connected to the electrical contact pads or conductors of the UVR circuit board 130.

In other examples, the UVR system 112 may be configured to be arranged between the shaft 22 of the light fixture 10 and an exposed surface of a ceiling, rafter or other structure (such as in a ceiling medallion or other mounting structure). In other examples, the UVR system 12 or 112 may be included in (as part of or selectively installed on) other types of overhead light fixtures, ceiling fans or combination light fixture/ceiling fans such as, but not limited to those described with reference to FIGS. 10-19, herein.

Figure 10:
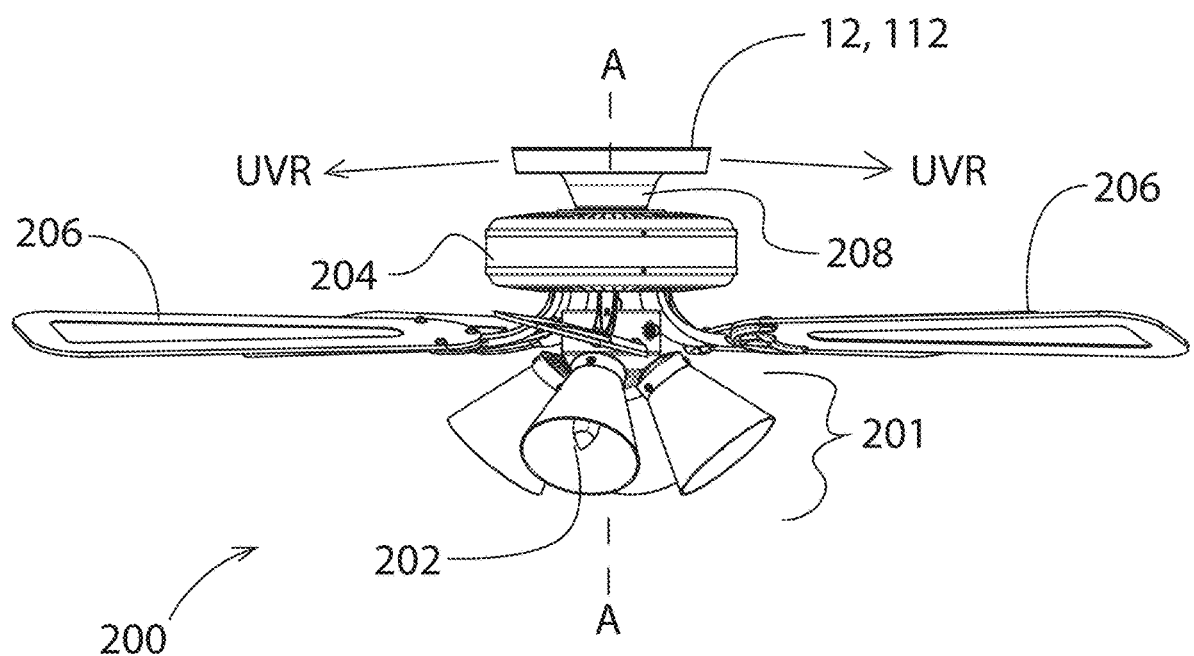
FIG. 10 is a side view of another example of a fixture having a UVR system.

In the example in FIG. 10, a UVR system 12 or 112 is included in a combination light fixture/ceiling fan system 200 that includes a light fixture 201 having one or more (three in FIG. 10) light sources 202 for emitting visible light, a fan motor 204 for rotating a set of fan blades 206 and a housing and mounting structure 208 for mounting and supporting the system 200 (including the fan motor 204 and fan blades 206) from a ceiling, rafter or other structure over a room space. The lighting sources 202 may include, but are not limited to one or more LED, incandescent, halogen, fluorescent, or other electronic light emitting devices, combinations thereof, or the like, for providing a visible light to illuminate a portion of a room or area.

The housing and mounting structure 208 may include a cylindrical (or other suitably shaped) outer body 214 adjacent to and supporting the UVR system 12 and 112 (similar to the manner in which the outer body 14 supports the UVR system 12 in the light fixture 10 of FIGS. 1-7). The outer body 214 of the mounting structure may be made of any suitable material including, but not limited to metal, plastic, wood, ceramic, composite materials or combinations thereof. However, in particular examples, the outer body 214 is made of a thermally conductive metal (or other thermally conductive material) and is arranged in heat transfer communication with the UVR circuit board of the UVR system 12, 112, to receive and dissipate heat from the UVR system 12, 112.

In certain examples, a connector (e.g., a lamp reducer, hickey, or other connector structure) extends from the housing and mounting structure 208 (e.g., through the central opening in the annual or ring-shaped body of the UVR system 12 or 112), for securing the system 200 to a ceiling, rafter or other structure over a room. In some examples, one or more electrical conductors extend through the connector and mounting structure 208, for providing electrical power or control signals (or both) to the UVR system 12, 112, the light fixture 202 and the fan motor 204. In some examples, the mounting structure 208 may include a ceiling medallion or housing that fits over the UVR system 12, 112, as a protective or decorative cover, and has one or more (or a plurality of) windows or openings through which UVR and visible light may pass.

In other examples, a UVR system 12, 112 may be part of or selectively installed on other ceiling fans (with or without a light fixture 202), or in other locations on the ceiling fan. In the system 200 and other systems having ceiling fans, the UVR system 12, 112 may be configured to emit UVR in a pattern as described with reference to FIG. 8 (or other suitable pattern), directed above the vertical height of the fan blades 206 and, thus, above the height of a human or animal in the room space.

Similar to certain examples described above, the pattern of UVR emitted by the UVR system 12, 112 in the system 200 may be located above a particular height (such as, but not limited to 7 feet, 8 feet, 9 feet, or other defined height from the floor or ground of the room space), to expose a volume of air within the room or space to UVR and to avoid direct exposure of UVR on people or animals in the room space. In some examples, the UVR is emitted at an angle (or slight angle) toward the ceiling, to avoid direct exposure of UVR on people or animals in the room space. In other examples, the UVR system is configured to emit UVC radiation (for example, but not limited to UVC within a wavelength of 200 nm. to 230 nm) in a direction that is at an angle (or slight angle) downward, away from the ceiling. In the system 200 and other systems having ceiling fans, the ceiling fan may help to circulate air within a room space, to cause more of the air within the room space to move into direct exposure to UVR emitted by the UVR system 12, 112, and to cause more of the air that has been exposed to UVR to move into lower regions of the room space.

Figure 11:
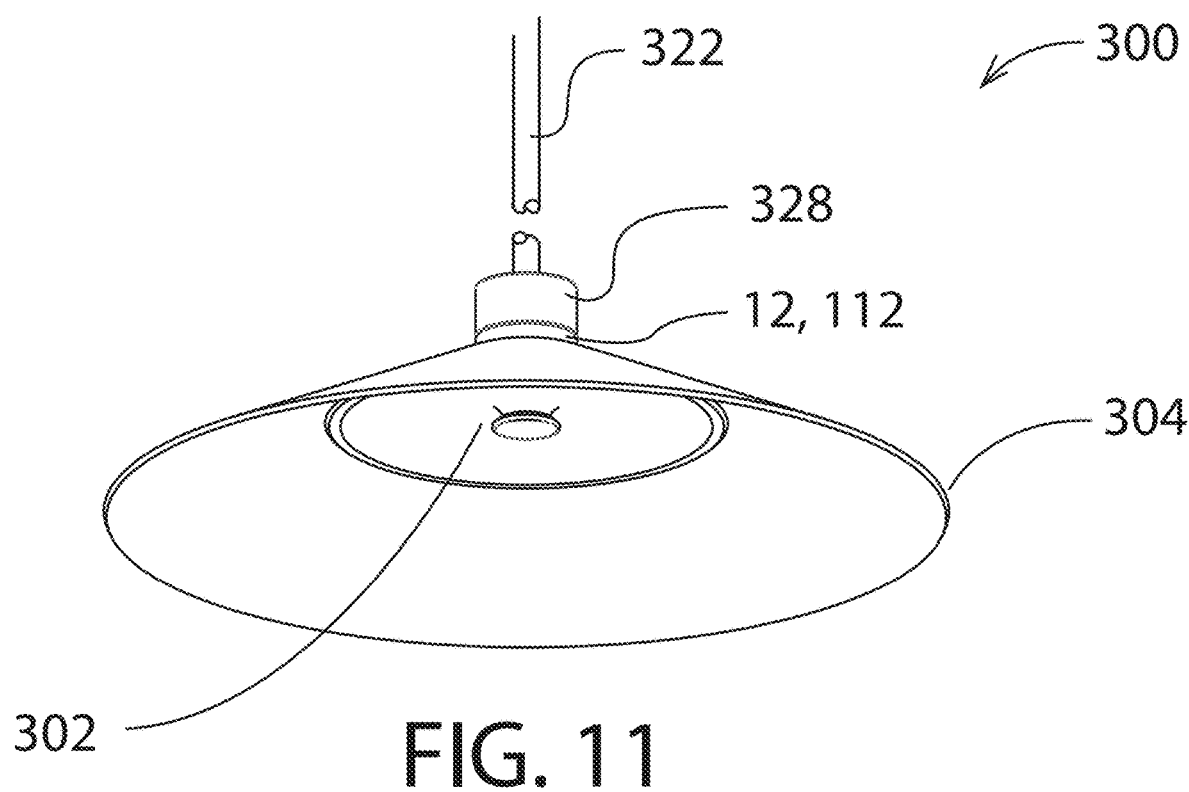
FIG. 11 is a perspective view of another example of a fixture having a UVR system.
Figure 12:
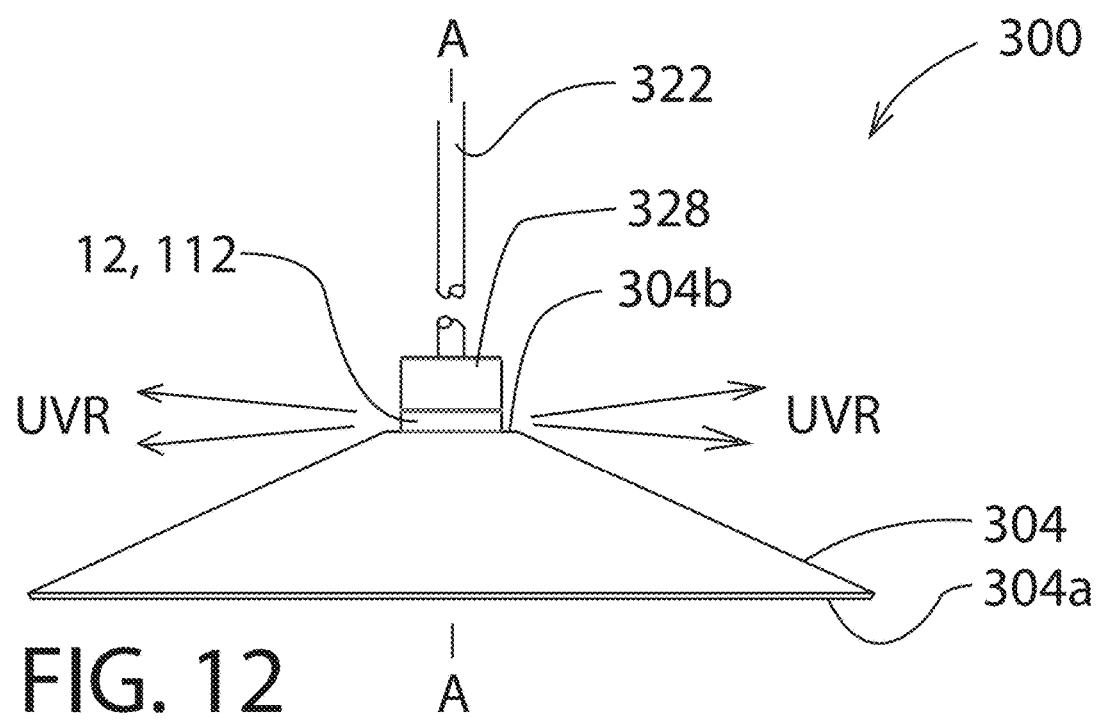
FIG. 12 is a side view of the fixture of FIG. 11.
Figure 13:
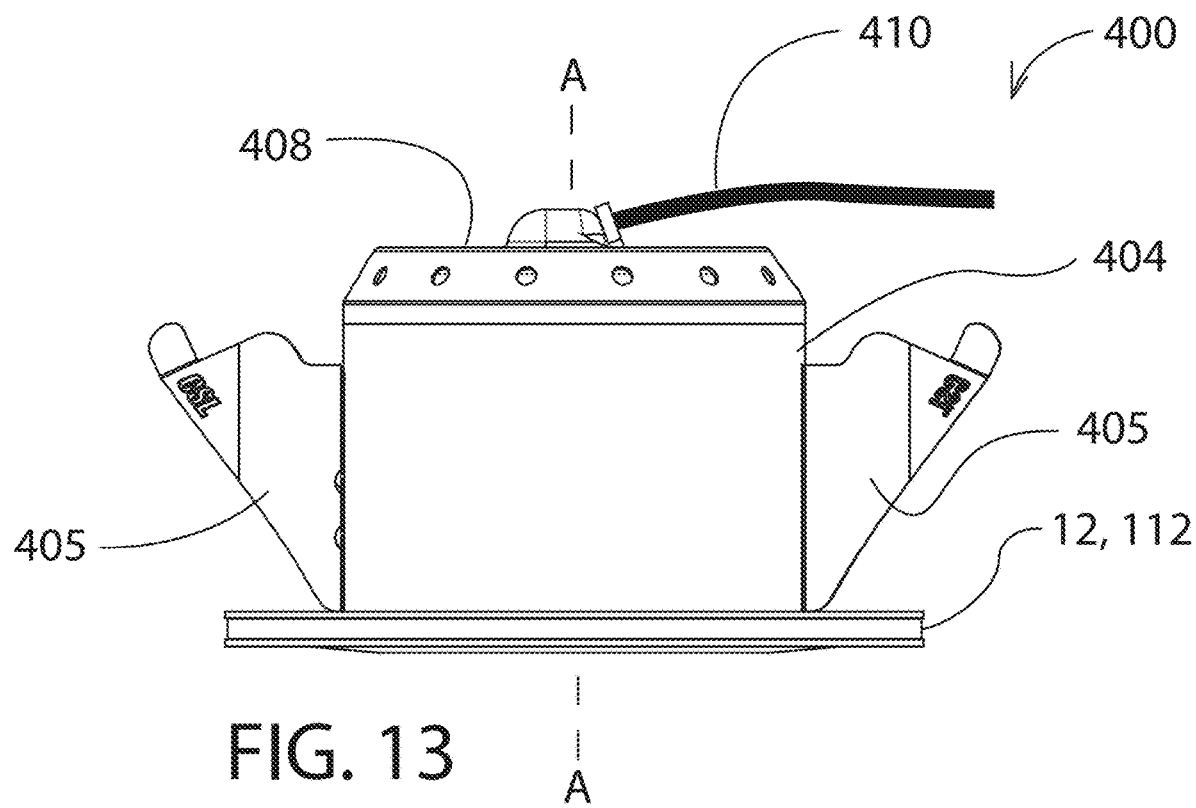
FIG. 13 is a side view of another example of a fixture having a UVR system.

In the example in FIGS. 11 and 12, a UVR system 12 or 112 is included in a light fixture 300 that has a light source 302 and an outer housing forming a shade 304 supported by a shaft 322, for example, from a ceiling, rafter, or other structure over a room or area space. The light source 302 may include one or more light emitting devices for emitting visible light, for illuminating a portion of the room or area such as, but not limited to one or more LED, incandescent, halogen, fluorescent, or other electronic light emitting devices, combinations thereof, or the like. The shade 304 includes a first end 304a (the downward-facing end in FIGS. 11 and 12) that defines an opening or optical passage through which light from the light source 302 may be emitted outward or downward.

A collar 328 may be located between the shaft 322 and the UVR system 12, 112. A connector (e.g., a lamp reducer, hickey or other connector) may extend from a second end 304b (the upward-facing end in FIGS. 11 and 12) of the shade 304. A threaded nut 326 may be connected to a threaded end of the connector, to secure the connector (and the shade 304) to the shaft 322. In certain examples, the shaft 322, the collar 328, the connector and the threaded nut 326 may be similar to or correspond to the shaft 22, the collar 28, the connector 24 and the threaded nut 26 discussed with regard to the fixture 10 in FIGS. 1-7. In particular examples, electrical conductors are connected to the light source 302 and to the UVR system 12, 112 and may extend through the shaft 322 (and through the connector and the collar 328), for providing electrical power or control signals (or both) to the UVR system 12, 112 and to the light source 302, such as discussed above with regard to conductors extending through the shaft 22, the connector 24, and the collar 28 of light fixture 10 in FIGS. 1-7.

In certain examples, the UVR system may be configured as an add-on or accessory (such as, but not limited to the UVR system 112) that can be selectively added (or not) to the light fixture 300, for example, between the collar 328 and the shade 304. In other examples, the UVR system may be configured to be included in a light fixture 300 as part of the fixture (e.g., built into the fixture as part of the original manufacture of the fixture), such as, but not limited to the UVR system 12.

The shade 304 of the light fixture 300 in FIGS. 11 and 12 forms an outer housing corresponding to the outer housing 14 of the light fixture 10 in FIGS. 1-7, but has a tapered or flared shape that tapers or flares outward at the first end 304a relative to a second end 304b. In other examples, the shade 304 may have other suitable shapes including dome shapes, semispherical shapes, cylindrical shapes, or the like. The shade may be made of any suitable material including, but not limited to metal, plastic, ceramic, wood, composite material, or combinations thereof. In particular examples, the shade 304 is made of one or more metal materials or other materials having good thermal conductivity and mass to receive, conduct and quickly dissipate heat generated by the lighting source 302 or the UVR system 12, 112 (or both).

In certain examples, the second end 304b of the shade 304 may be closed (similar to the closed end 14b of the outer housing 14) and defines an outer surface (facing upward in FIGS. 11 and 12) on which a bracket for holding an UVR circuit board may be disposed (for example, similar to or corresponding to the bracket 36 and UVR circuit board 30 of the UVR system 12 in light fixture 10 of FIGS. 1-7). In other examples, an add-on or accessory UVR system 112 may be disposed and supported on the closed end 304b of the shade 304. In either of those examples, the light source 302 may include one or more LED light sources (or one or more circuit boards having one or more LED light sources) that are mounted in direct contact or in other heat transfer communication with an inner surface of the closed second end 304b of the shade 304. In yet other examples, the second end 304b of the shade 304 may be open or may receive an end of the light source 302 in an opening. In those and other examples, the light source 302 or the UVR circuit board of the UVR system 12, 112 (or both the light source and the UVR circuit board) may be arranged in direct contact or other thermal conductivity with the shade 304, such that heat may transfer from the light source 302 or the UVR circuit board (or both) to the shade 304 and may be conducted and dissipated in the shade 304 and the environment around the shade 304.

In the example of FIGS. 11 and 12, the light fixture 300 may be installed in a room or area, and operated to emit light from the light source 302 downward, into the room or area, to illuminate a portion of the room or area. In addition, the light fixture 300 may be operated to emit UVR from the UVR system 12, 112, where the UVR is emitted generally horizontally or at an upward angle, above the shade 304 of the light fixture 300. Similar to certain examples described above, the pattern of UVR may be located above a particular height (such as, but not limited to 7 feet, 8 feet, 9 feet, or other defined height from the floor or ground of the room space), to expose a volume of air within the room or space to UVR and to avoid direct exposure of UVR on people or animals in the room space. In some examples, the UVR is emitted at an angle (or slight angle) toward the ceiling. In other examples, the UVR system is configured to emit UVC radiation (for example, but not limited to UVC within a wavelength of 200 nm. to 230 nm) in a direction that is at an angle (or slight angle) downward, away from the ceiling.

In the example in FIGS. 13-16, a UVR system 12 or 112 is included in a downlight light fixture 400 that is configured to be mounted within an aperture in a ceiling, wall or other structure. In certain examples, the UVR system in a downlight light fixture 400 may be configured as an add-on or accessory (such as, but not limited to the UVR system 112) that can be selectively added (or not) to the light fixture 400. In other examples, the UVR system may be configured to be included in a light fixture 400 as part of the fixture (e.g., built into the fixture as part of the original manufacture of the fixture), such as, but not limited to the UVR system 12.

The downlight fixture 400 includes a light source 402 contained within an outer housing 404. The outer housing 404 may have a cylindrical shape or any other suitable shape and is configured to be received within an aperture in a ceiling, wall or other structure. One or more clips 405 (two shown in FIGS. 13-16) are attached to the outer housing 404, to help secure the outer housing 404 within the aperture in the ceiling, wall or other structure.

The outer housing 404 has a first end 404a through which light from the light source 402 may pass. An annular flange or bezel 406 may be connected to the outer housing 404 at or adjacent the first end 404a. The flange 406 is configured to reside on the exposed side of a ceiling, wall or other structure, for example, to provide an ornamental or decorative appearance, when the outer housing is installed in the ceiling, wall or other structure. In certain examples, the downlight fixture 400 is configured to be installed in a manner such that the flange 406 appears flush or substantially flush with an exposed surface of the ceiling, wall or other object, when installed. In other examples, variations of the downlight fixture may be configured to be installed in a manner that is not flush with the exposed surface (e.g., recessed, or protruding from the exposed surface) of the ceiling, wall or other object, is surface-mounted on the exposed surface of the ceiling, wall or other object, or is mounted on a support structure (such as, but not limited to a sconce structure, pedestal, shaft or the like).

The light source 402 may include one or more light emitting devices such as, but not limited to one or more LED, incandescent, halogen, fluorescent, or other electronic light emitting devices, combinations thereof, or the like. In particular examples, the light source includes one or more LEDs (or circuit boards having one or more LEDs) that are in contact with or other heat transfer communication with the outer housing 404, to transfer heat from the LEDs to the outer housing 404 and to the flange 406.

The outer housing 404 has a second end 404b on which a cap 408 is attached and through which electrical conductors 410 may extend. The electrical conductors 410 are connected to the light source 402 and to the UVR system 12, 112, for providing electrical power or control signals (or both) to the light source 402 or the UVR system 12, 112 (or both).

The outer housing 404 and the flange 406 may be made of any suitable materials or combinations of materials including, but not limited to metal, plastic, ceramic, wood, composite material, or combinations thereof. In particular examples, the outer housing 404 and the flange are each made of one or more metal materials or other materials having good thermal conductivity and mass to receive, conduct and quickly dissipate heat generated by the lighting source 402 or the UVR system 12, 112 (or both).

Figure 16:
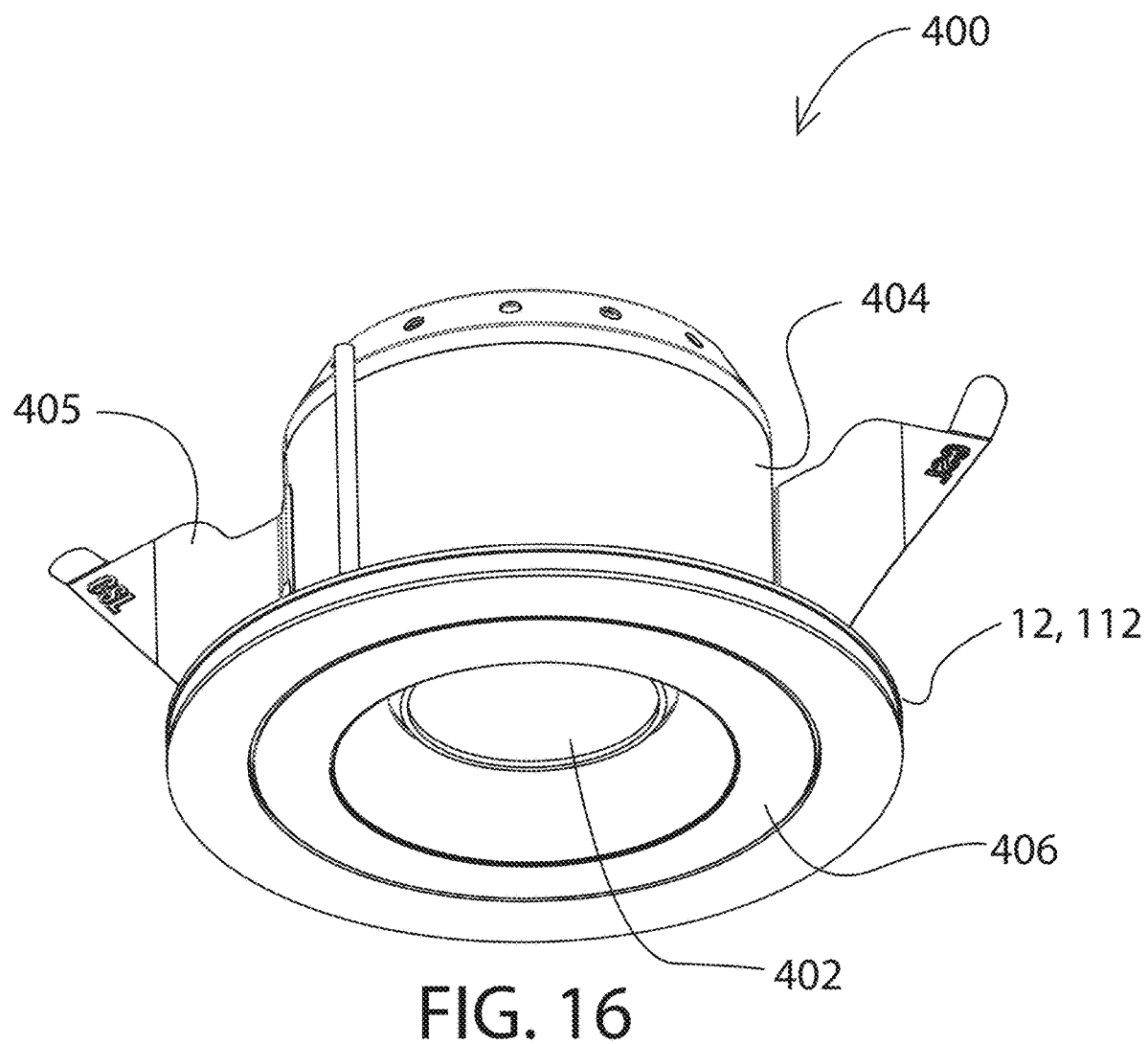
FIG. 16 is a perspective view of the fixture of FIG. 13 with the UVR system attached.
Figure 17:
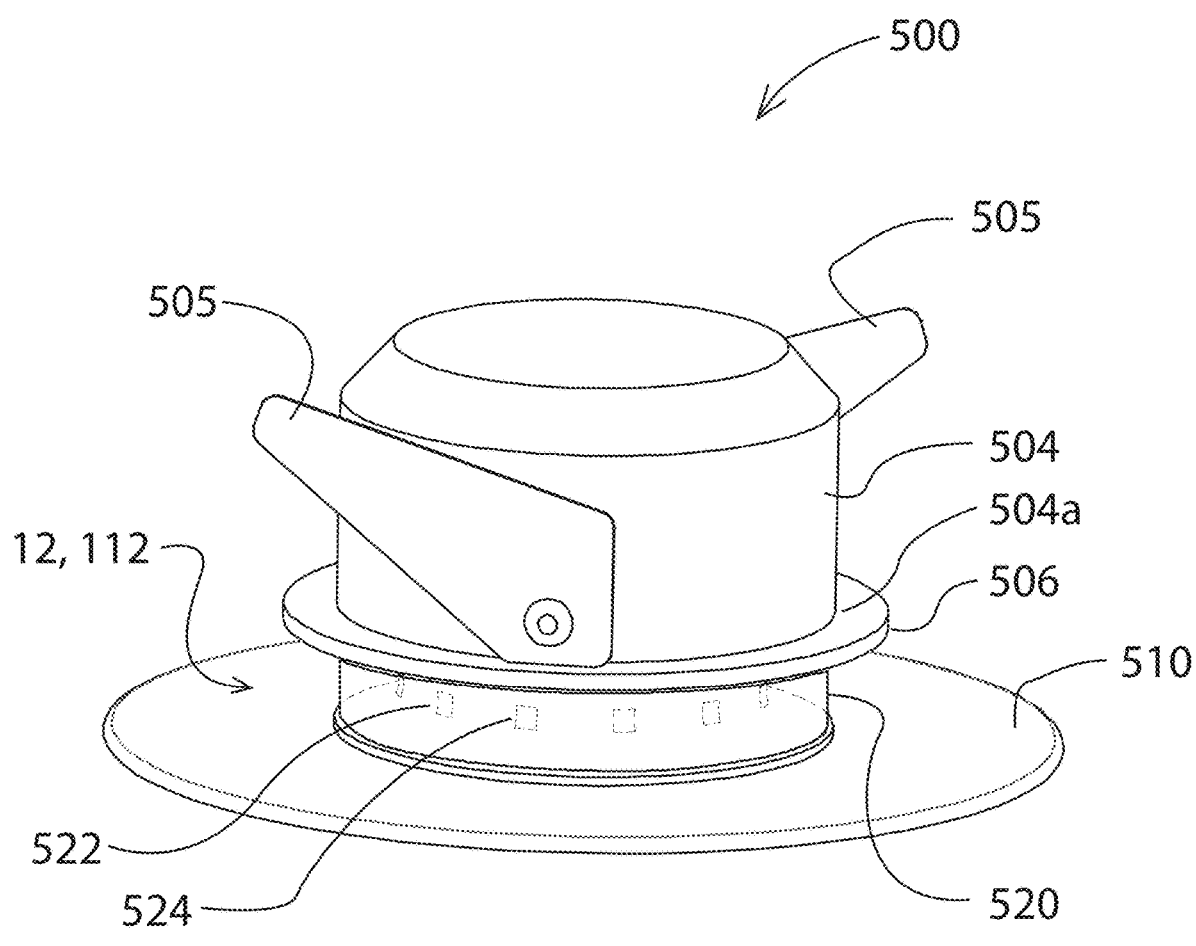
FIG. 17 is a perspective view of another example of a fixture having a UVR system.
Figure 18:
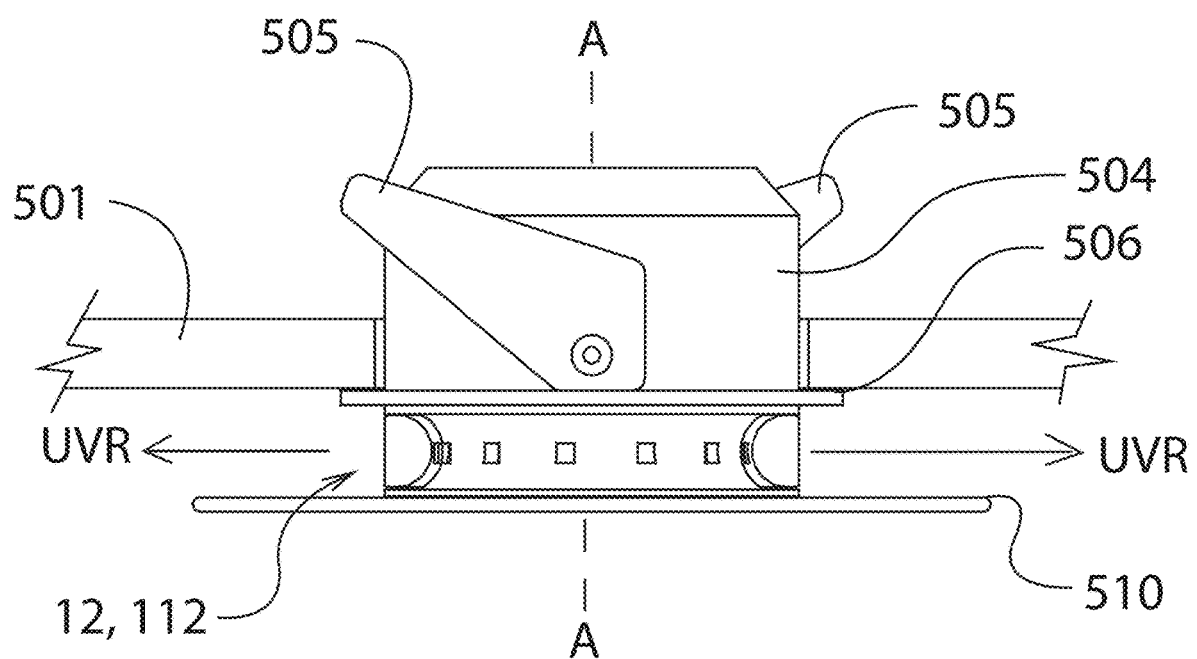
FIG. 18 is a side view of the fixture of FIG. 17.

In certain examples, the downlight fixture 400 may have a configuration corresponding to the lighting device assembly 1600 or the lighting device assembly 1800 in FIGS. 16-18 of U.S. patent application Ser. No. 16/808,102, titled Adjustable Lighting Device (which is incorporated herein by reference, in its entirety). In other examples, the downlight fixture 400 may have other suitable configurations. However, the downlight fixture 400 further includes the UVR system 12, 112.

Figure 14:
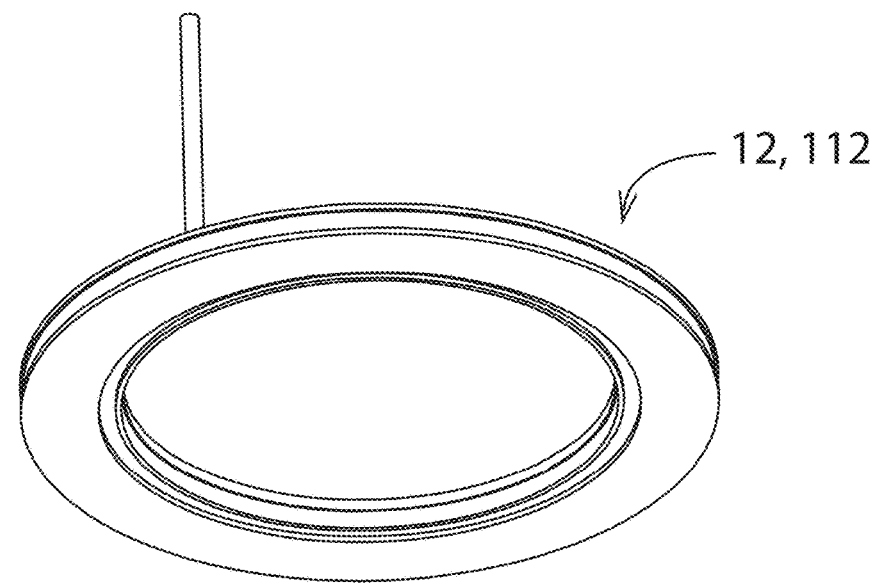
FIG. 14 is a perspective view of a UVR system of the fixture of FIG. 13.

An example of a UVR system 12, 112 for the downlight fixture 400 is shown in FIG. 14. In certain examples, the UVR system in FIG. 14 may be similar to or correspond to the UVR system 112 described with reference to FIG. 9. In certain examples, the UVR system 12, 112 is attached to (or attachable to) the flange 406 of the downlight fixture 400. In particular examples, the outer housing 404 may be received and mounted within an opening in a ceiling, wall or other structure, while the flange 406 and the UVR system 12, 112 is located on the exposed side of the ceiling, wall or other structure.

Figure 15:
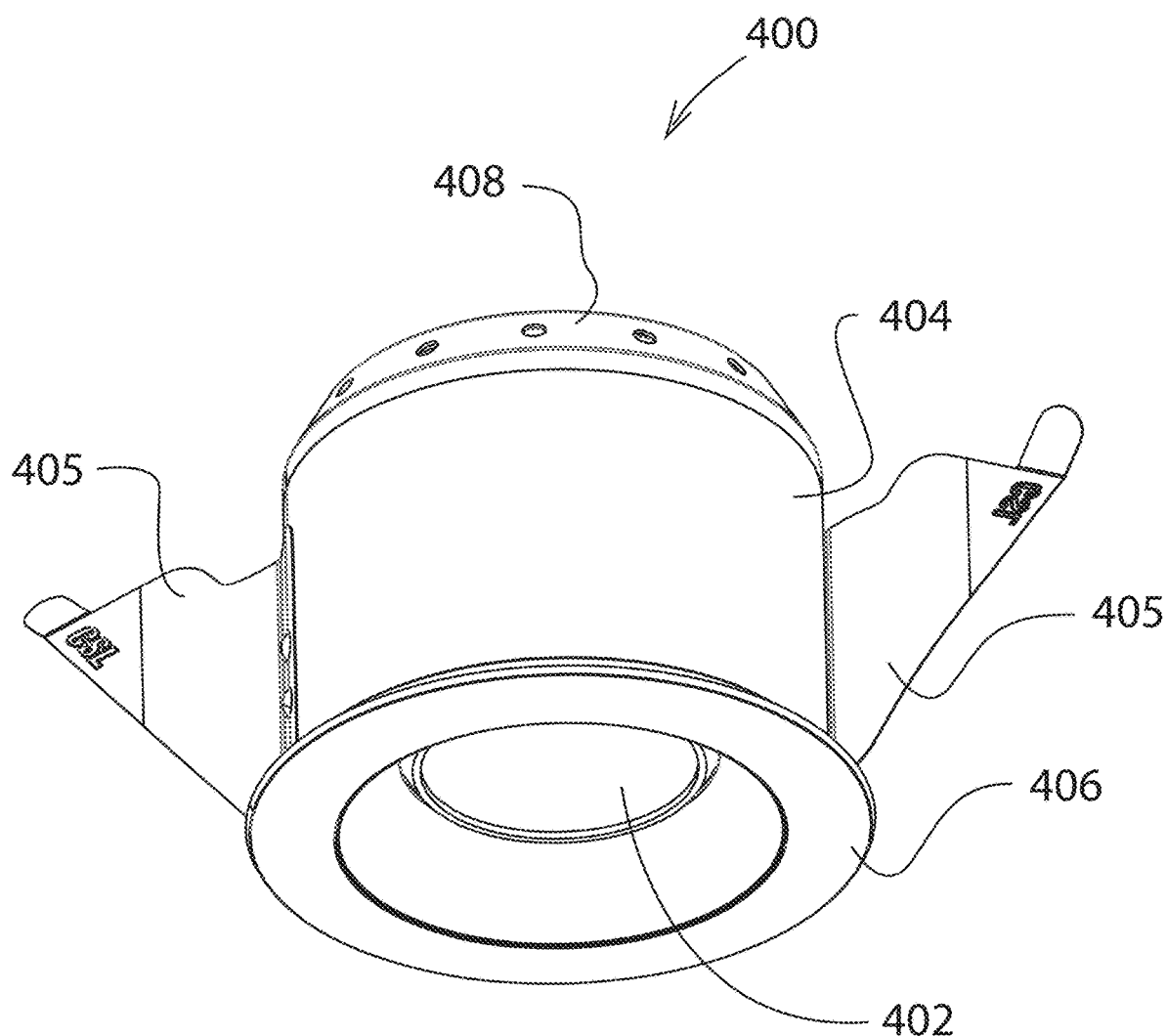
FIG. 15 is a perspective view of the fixture of FIG. 13 without or before the UVR system is attached thereto.

In certain examples, the UVR system 12, 112 has an annular body that is configured to fit around and secure to an outer peripheral edge or surface of the flange 406. The downlight fixture 400 is shown in FIG. 15 without the UVR system 12, 112 attached to the flange 406, and is shown in FIG. 16 with the UVR system 12, 112 attached to the flange 406. The UVR system 12, 112 may be attached and secured to the flange 406 in any suitable manner including, but not limited to a friction fit, one or more fasteners, clips, adhesive material, welds, solder, or the like. In particular examples, the UVR system 12, 112 is configured to be selectively connected and disconnected from the flange 406, to selectively convert the fixture 400 into a UVR emitting system. In certain examples, the UVR system 12, 112 is provided in an annular collar that connects around and to the periphery of the flange 406, and has one or more conductors connected to (or configured to connect to) one or more separate power supply conductors relative to the light source 402.

In the example of FIGS. 13-16, the light fixture 400 may be installed in an opening in a ceiling, wall or other structure of a room or area, and operated to emit light from the light source 402 downward, into the room or area, to illuminate a portion of the room or area. In addition, the light fixture 400 may be operated to emit UVR from the UVR system 12, 112, where the UVR is emitted generally horizontally or at an upward angle, above the bottom edge of the flange 406 of the light fixture 400. Similar to certain examples described above, the pattern of UVR may be located above a particular height (such as, but not limited to 7 feet, 8 feet, 9 feet, or other defined height from the floor or ground of the room space), to expose a volume of air within the room or space to UVR and to avoid direct exposure of UVR on people or animals in the room space. In some examples, the UVR is emitted at an angle (or slight angle) toward the ceiling. In other examples, the UVR system is configured to emit UVC radiation (for example, but not limited to UVC within a wavelength of 200 nm. to 230 nm) in a direction that is at an angle (or slight angle) downward, away from the ceiling.

In the example in FIGS. 17-18, a UVR system 12 or 112 is included in a fixture 500 that is configured to be mounted within an aperture in a ceiling, wall or other structure, similar to the manner in which the downlight fixture 400 is mounted, as described herein. The fixture 500 is shown in FIG. 18, in an installed state, within a panel 501 of a ceiling, wall or other structure. However, unlike the downlight fixture 400, the fixture 500 does not include a light source that emits visible light directly downward (as does light source 402 of the downlight fixture 400). Instead, the UVR system 12, 112 in the fixture 500 includes one or more (or a plurality of) light emitting devices that emit visible light generally horizontally or at an upward angle, in addition to one or more UVR emitting devices as described herein. In some examples, the visible light is emitted in the same direction or pattern (or generally the same direction or pattern) as the UVR from the UVR system 12, 112. In other examples, the visible light is emitted generally horizontally and at an upward angle, but at a different angle or pattern than that of the UVR from the UVR system 12, 112 in the fixture 500.

In certain examples, the UVR system in a fixture 500 may be configured as an add-on or accessory (such as, but not limited to the UVR system 112) that can be selectively added (or not) to the fixture 500. In other examples, the UVR system may be configured to be included in a fixture 500 as part of the fixture (e.g., built into the fixture as part of the original manufacture of the fixture), such as, but not limited to the UVR system 12.

The fixture 500 includes an outer housing 504 that may have a cylindrical shape or any other suitable shape, and is configured to be received within an aperture in a ceiling, wall or other structure. One or more clips 505 (two shown in FIGS. 17-18) are attached to the outer housing 504, to help secure the outer housing 504 within the aperture in the ceiling, wall or other structure. In certain examples, the outer housing 504 is similar to or corresponds to the outer housing 404 of the downlight fixture 400 in FIGS. 13-16.

An annular flange or bezel 506 may be connected to the outer housing 504 at or adjacent a first end 504a. The flange 506 is configured to reside on the exposed side of a ceiling, wall or other structure, for example, to provide an ornamental or decorative appearance, when the outer housing is installed in the ceiling, wall or other structure. In certain examples, the fixture 500 is configured to be installed in a manner such that the flange 506 appears flush or substantially flush with an exposed surface of the ceiling, wall or other object, when installed. In other examples, variations of the fixture may be configured to be installed in a manner that is not flush with the exposed surface (e.g., recessed, or protruding from the exposed surface) of the ceiling, wall or other object, is surface-mounted on the exposed surface of the ceiling, wall or other object, or is mounted on a support structure (such as, but not limited to a sconce structure, pedestal, shaft or the like).

The outer housing 504 has a second end 504b on which a cap 508 is attached and through which electrical conductors may extend. The electrical conductors are connected to the UVR system 12, 112, for providing electrical power or control signals (or both) to the UVR system 12, 112. In certain examples, the cap 508 and the electrical conductors are similar to or corresponds to the cap 408 and the electrical conductors 410 of the downlight fixture 400 in FIGS. 13-16.

The outer housing 504 and the flange 506 may be made of any suitable materials or combinations of materials including, but not limited to metal, plastic, ceramic, wood, composite material, or combinations thereof. In particular examples, the outer housing 504 and the flange are each made of one or more metal materials or other materials having good thermal conductivity to receive, conduct and quickly dissipate heat generated by the UVR system 12, 112.

In certain examples, the UVR system in the fixture 500 may be similar to or correspond to the UVR system 112 described with reference to FIG. 9 or 14. In certain examples, the UVR system 12, 112 is attached to (or attachable to) the flange 506 of the fixture 500. In particular examples, the outer housing 504 may be received and mounted within an opening in a ceiling, wall or other structure, while the flange 506 and the UVR system 12, 112 is located on the exposed side of the ceiling, wall or other structure.

In certain examples, the UVR system 12, 112 has a disc shaped or an annular body. The body of the UVR system 12, 112 has a first end (facing upward in FIGS. 17 and 18) that is configured to secure to the flange 506. The UVR system 12, 112 may be attached and secured to the flange 506 in any suitable manner including, but not limited to a friction fit, one or more fasteners, clips, adhesive material, welds, solder, or the like. In particular examples, the UVR system 12, 112 is configured to be selectively connected and disconnected from the flange 506, to selectively convert the fixture 500 into a UVR emitting system. In certain examples, the UVR system 12, 112 is provided in an annular collar that connects around and to the periphery of the flange 506, and has one or more conductors connected to (or configured to connect to) one or more power supply conductors.

The fixture 500 also includes a light baffle member 510 that is attached to a second end (facing downward in FIGS. 17 and 18) of the body of the UVR system 12, 112. The light baffle member 510 may have a plate or disc-like shape, or any other suitable shape, to extend laterally outward relative to the second end of the UVR system 12, 112. The light baffle member 510 is made of any suitable material including, but not limited to metal, plastic, ceramic, wood, composite material, or combinations thereof. In particular examples, the light baffle member 510 is made of a material, or has a coating or layer of material on the surface facing the direction of the UVR system 12, 112 (i.e., the upward facing surface of the light baffle member 510 in FIGS. 17 and 18) that absorbs or reflects UVR and visible light emitted from the UVR sources and visible light sources in the UVR system 12, 112.

In the example of FIGS. 17-18, the fixture 500 may be installed in an opening in a ceiling, wall or other structure of a room or area, and operated to emit visible light and to emit UVR from the UVR system 12, 112, where the visible light and the UVR are emitted generally horizontally or at an upward angle, above the bottom edge of the baffle member 510 of the light fixture 500. Similar to certain examples described above, the pattern of UVR may be located above a particular height (such as, but not limited to 7 feet, 8 feet, 9 feet, or other defined height from the floor or ground of the room space), to expose a volume of air within the room or space to UVR and to avoid direct exposure of UVR on people or animals in the room space. In some examples, the UVR is emitted at an angle (or slight angle) toward the ceiling.

The baffle member 510 extends sufficiently outward (in a direction perpendicular to or transverse to the axis A) to block any visible light or UVR that may be directed or reflected directly downward. As a result, the visible light can create a halo effect.

In certain examples of the fixture 500 (or of the fixtures 10, 200, 300, or 400), the UVR system 12, 112 may include an outer housing or shell 520 having one or more (or a plurality of) windows 522 through which UVR and one or more (or a plurality of) windows 524 through which visible light from one or more visible light sources are arranged to emit radiation.

Figure 19:
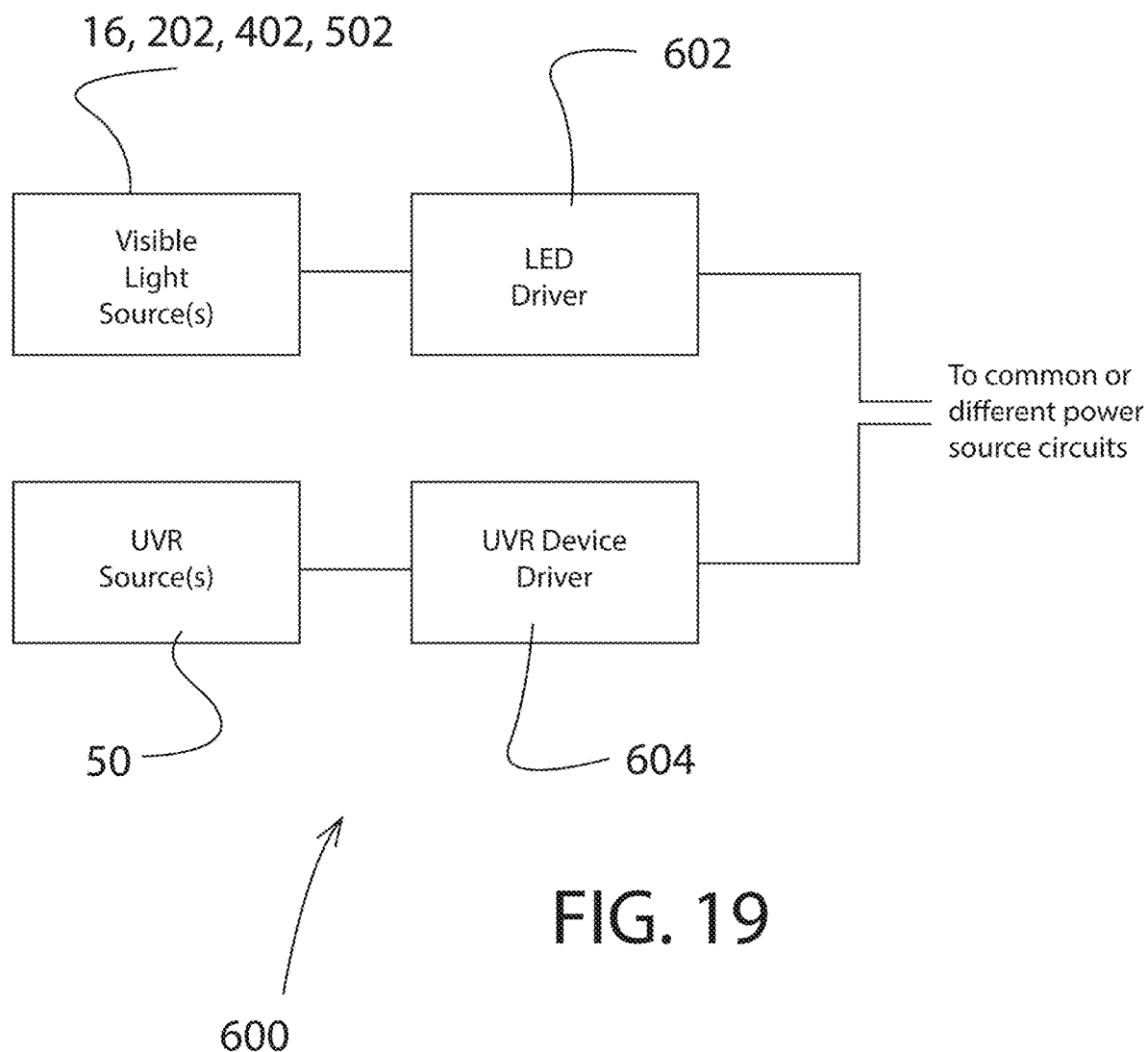
FIG. 19 is a generalized electrical schematic for a fixture according to various examples.

A generalized diagram of an electrical circuit 600 for providing electrical power or control signals (or both) to visible light sources and to UVR sources in the fixtures 10, 200, 300, 400 or 500 is shown in FIG. 19. In certain examples, the electrical circuit 600 includes one or more first driver circuits 602 electrically coupled for providing electrical power or control signals (or both) to one or more visible light sources in the fixture, and one or more second driver circuits 604 electrically coupled for providing electrical power or control signals (or both) to one or more UVR sources in the UVR system 12, 112 of the fixture. In some examples, the drivers 602 and 604 may be electrically connected to receive electrical power from a common electrical power source or circuit. In other examples, the drivers 602 and 604 are electrically connected to mutually separate electrical power sources or electrical circuits.

In various examples described herein, certain components are described as having a round shape, disc shape, or cylindrical shaped portions. However, in other examples, those components may have other suitable shapes including, but not limited to shapes having polygonal or other non-circular cross-sections (taken perpendicular to the axis A) or combinations thereof. In some examples, those components may have an outer shape configured to provide an aesthetically pleasing, artistic, industrial or other impression.

The foregoing description of illustrative embodiments has been presented for purposes of illustration and of description. It is not intended to be exhaustive or limiting, and modifications and variations may be possible in light of the above teachings or may be acquired from practice of the disclosed embodiments. Various modifications and changes that come within the meaning and range of equivalency of the claims are intended to be within the scope of the invention. Thus, while certain embodiments of the present invention have been illustrated and described, it is understood by those of ordinary skill in the art that certain modifications and changes can be made to the described embodiments without departing from the spirit and scope of the present invention as defined by the following claims, and equivalents thereof.

What is claimed is:

1. A fixture system comprising:
 a housing configured to be mounted in an upper region of a room or area;
 a light source supported by the housing for providing visible light to illuminate at least a portion of the room or area; and
 an ultraviolet radiation (UVR) system supported by the housing for emitting UVC radiation having one or more wavelengths within the range of 200 nm. to 290 nm. in an upper region of the room or area.

2. The fixture system of claim 1, wherein the light source is supported by the housing to emit visible light in a downward direction or downward angled direction within the room or area and wherein the UVR system is supported by the housing to emit the UVC radiation in a horizontal direction or in an upward angled direction within the room or area.

3. The fixture system of claim 1, wherein the UVR system includes at least one UVC emitting source and an optic member configured to direct the UVC radiation from the at least one UVC emitting source in a pattern having a vertical width dimension that is above a threshold height from a floor or ground in the room or area.

4. The fixture system of claim 1, wherein the UVR system includes at least one UVC emitting source.

5. The fixture system of claim 1, wherein the UVR system includes an optic member and a circuit board, the circuit board having substrate on which a plurality of UVC emitting LEDs are mounted for emitting the UVC radiation toward the optic member, the optic member configured to emit the UVC radiation in a horizontal direction or in an upward angled direction within the room or area.

6. The fixture system of claim 5, further comprising a bracket attached to the housing and configured to receive and hold the circuit board of the UVR system, the bracket configured to allow selective removal of the circuit board from the bracket for service, inspection or replacement.

7. The fixture system of claim 6, wherein the housing has a first end having an opening or optical passage arranged to pass light from the light source, the housing has a second end on which the bracket is attached, and the second end of the housing faces opposite to the first end of the housing.

8. The fixture system of claim 6, further comprising a shaft for supporting the housing from a ceiling, wall or other structure, wherein the circuit board extends partially around the shaft and has a gap to pass the shaft as the circuit board is moved into or out from the bracket.

9. The fixture system of claim 6, further comprising a shaft for supporting the housing from a ceiling, wall or other structure, the shaft extending in a direction of an axis A of the housing, wherein the circuit board is selectively moveable into or out of the bracket in a direction that is transverse to the axis A.

10. The fixture system of claim 5, wherein the UVR system is configured to be selectively added onto or removed from the housing, as an add-on accessory.

11. The fixture system of claim 5, wherein the optic member and the circuit board of the UVR system are attached together as to form a one-piece, unitary structure that can be selectively added onto or removed from the housing.

12. The fixture system of claim 5, wherein the optic member comprises a body of quartz, fused quartz, or fused silica.

13. The fixture system of claim 5, wherein the circuit board of the UVR system further includes at least one light emitting source for emitting visible light in a horizontal direction or in an upward angled direction within the room or area.

14. The fixture system of claim 13, wherein the UVR system includes at least one UVC emitting source and an optic member configured to direct the UVC radiation from the at least one UVC emitting source in a pattern having a vertical width dimension that is above a threshold height from a floor or ground in the room or area.

15. The fixture system of claim 1, wherein the UVR system includes a circuit board on which at least one UVC emitting device is mounted, the circuit board being in thermal communication with the housing to transfer heat from the UVC emitting device to the housing for dissipation in or from the housing.

16. The fixture system of claim 15, wherein the light source is supported in the housing to emit visible light in a downward direction or downward angled direction within the room or area and wherein the light source is in thermal communication with the housing to transfer heat from the light source to the housing for dissipation in or from the housing.

17. The fixture system of claim 1, further comprising a flange member on a first end of the housing, wherein the housing is configured to be received within a hole in a ceiling, in a wall or in another structure, while the flange member is located on an exposed side of the ceiling, of the wall or of the other structure, and wherein the UVR system is attached to the flange member.

18. The fixture system of claim 1, further comprising a fan motor and fan blades supported by the housing below the UVR system.

19. A fixture system comprising:
a housing configured to be mounted in an upper region of a room or area;
an ultraviolet radiation (UVR) system supported by the housing and having at least one UVR emitting source and an optic member for emitting UVC radiation in an upper region of the room or area, in a horizontal direction or in an upward angled direction within the room or area;
a flange member on a first end of the housing;
wherein the housing is configured to be received within a hole in a ceiling, in a wall or in another structure, while the flange member is configured to be located on an exposed side of the ceiling, of the wall or of the other structure; and
wherein the UVR system is attached to the flange member to be located on the exposed side of the ceiling, of the wall or of the other structure.

20. The fixture system of claim 1, further comprising a baffle member attached to the UVR system to block the UVC radiation and visible light from passing in a vertical direction relative to the UVR system; wherein the UVR system further includes at least one a light source configured to emit visible light in the horizontal direction or in the upward angled direction within the room or area, above the baffle member.

* * * * *